United States Patent
Mabuchi et al.

(10) Patent No.: US 6,936,148 B2
(45) Date of Patent: Aug. 30, 2005

(54) GAS SENSOR ELEMENT HAVING AT LEAST TWO CELLS

(75) Inventors: Tomohiro Mabuchi, Aichi (JP); Yoshiaki Kuroki, Aichi (JP); Shinya Awano, Aichi (JP); Hiroyuki Hayashi, Aichi (JP); Kunio Yanagi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 501 days.

(21) Appl. No.: 10/270,292

(22) Filed: Oct. 15, 2002

(65) Prior Publication Data

US 2003/0183520 A1 Oct. 2, 2003

(30) Foreign Application Priority Data

Mar. 29, 2002 (JP) ........................................ 2002-097563

(51) Int. Cl.[7] ........................ G01N 27/409; G01N 27/41
(52) U.S. Cl. ........................ 204/425; 204/426; 204/428; 73/23.32
(58) Field of Search ................................ 204/424, 425, 204/426, 427, 428, 429; 205/784, 785; 73/23.31, 23.32

(56) References Cited

U.S. PATENT DOCUMENTS

| | | | | |
|---|---|---|---|---|
| 4,264,425 A | * | 4/1981 | Kimura et al. ............... 204/412 |
| 4,505,807 A | * | 3/1985 | Yamada ....................... 204/425 |
| 4,647,364 A | * | 3/1987 | Mase et al. .................. 204/427 |
| 6,007,688 A | * | 12/1999 | Kojima et al. .............. 204/426 |
| 6,007,697 A | * | 12/1999 | Yagi et al. ................... 205/788 |
| 6,153,071 A | * | 11/2000 | Omara et al. ............... 204/424 |

* cited by examiner

*Primary Examiner*—Kaj K. Olsen
(74) *Attorney, Agent, or Firm*—Sughrue Mion, PLLC

(57) ABSTRACT

A sensor element including an insulative base (11), a heating resistor (12), an oxygen pump cell (13), an oxygen detection cell (14), and a diffusion-chamber-forming member (161) having a rate-controlling introduction portion (163) and defining a diffusion chamber (16) in cooperation with electrodes (1321, 1421), wherein these components have been subjected to simultaneous firing (i.e., cofiring) to form a unitary sensor element. A partition wall (162), which extends from the diffusion-chamber-forming member and is made of alumina, is joined to a surface of a solid electrolyte (131) between two electrodes (1321, 1322) of an Ip cell. Preferably, a region within 20 μm from the plane of junction joining the partition wall (162) to the solid electrolyte (131) contains no portion whose amount of non-alumina substances exceeds by 2% by mass (by weight) or more the amount of non-alumina substances of the diffusion-chamber-forming member (161).

16 Claims, 14 Drawing Sheets

GAS SENSOR ELEMENT HAVING AT LEAST TWO CELLS

BACKGROUND OF THE INVENTION

1. Field of the Invention

The present invention relates to a gas sensor element and a gas sensor using the same, more particularly, to a gas sensor element having at least two-cell configuration suitable for use as, for example, a full-range air-fuel ratio sensor (a sensor capable of measuring air-fuel ratio of an internal combustion over the entire range thereof), a nitrogen oxide gas sensor, a flammable gas sensor (a sensor capable of measuring carbon monoxide, hydrocarbon gas, or other flammable gas), or a compound gas sensor (a sensor capable of measuring a plurality of gases selected from among oxygen, nitrogen oxides, carbon monoxide, hydrocarbon gas, and other flammable gases).

2. Description of the Related Art

Increasingly strict regulations have been imposed on the emission quantity of harmful matter (e.g., hydrocarbon gas, carbon monoxide, and nitrogen oxides) contained in exhaust gas discharged from an internal combustion engine of an automobile, etc. Moreover, in view of the greenhouse effect and other problems, the necessity to reduce the emission of carbon dioxide has arisen, thereby raising an urgent need for a method of further reducing consumption of fuel by internal combustion engines.

Under such circumstances, more strict requirements have been imposed on gas sensors, which are indispensable to reduction of harmful matter contained in exhaust gas and improvement of fuel efficiency, and gas sensors having improved performance and reliability are demanded. In particular, in recent years, demand has arisen for a gas sensor which can be activated quickly and can save electric power, while having improved performance and reliability. Moreover, carbon monoxide gas sensors and nitrogen oxide gas sensors capable of directly detecting harmful components themselves have attracted a great deal of attention.

The below-mentioned patent documents 1 and 2 and other documents disclose a two-cell-type gas sensor element which includes an oxygen pump cell having a pair of electrodes provided on a solid electrolyte layer, and an oxygen detection cell having a similar configuration. The gas sensor element enables full-range measurement of air-fuel ratio of an internal combustion engine of, for example, an automobile, to thereby improve fuel efficiency of the internal combustion engine. In a gas sensor element of such a type, ions such as oxygen ions must quickly move through the solid electrolyte layer. Therefore, a heating resistor for heating the solid electrolyte layer is disposed in the vicinity of the cells in order to heat and maintain the oxygen pump cell at a temperature of, for example, 700° C. or higher. However, since ceramic material which constitutes the solid electrolyte generally has low thermal conductivity, the operation of heating the cells to high temperature for, in particular, quick activation of the cells cannot be performed quickly and efficiently. Moreover, since use of a large amount of expensive zirconia material increases the cost of such a gas sensor, the range of application thereof is limited, even though such a gas sensor exhibits excellent performance.

Notably, the below-mentioned patent documents 3 and 4 disclose a technique for simultaneously firing zirconia ceramic and alumina ceramic. Moreover, the below-mentioned patent document 5 discloses a technique for preventing migration.

[Patent Document 1]
Japanese Patent Application Laid-Open No. 62-148849
[Patent Document 2]
Japanese Patent Application Laid-Open No. 11-14594
[Patent Document 3]
Japanese Patent Application Laid-Open No. 2001-66280
[Patent Document 4]
Japanese Patent Application Laid-Open No. 2000-292406
[Patent Document 5]
Japanese Patent Application Laid-Open No. 62-44971

3. Problems Solved by the Invention

Among the above-described problems, the problem in relation to heating efficiency can be solved by a gas sensor element disclosed in patent document 2. The gas sensor element utilizes a substrate in which a heating resistor is embedded in a ceramic material that contains alumina, having excellent thermal conductivity, as a predominant component. However, this gas sensor has the following drawback. Since the substrate is formed of alumina which greatly differs in thermal expansion from zirconia that is used as a material for a solid electrolyte layer, when the substrate and the solid electrolyte layer are joined through simultaneous firing, cracks are generated in the solid electrolyte layer or the solid electrolyte layer is broken into pieces. Further, patent documents 4 and 5 disclose a gas sensor that is fabricated through simultaneous firing (namely cofiring) of an alumina substrate and a solid electrolyte layer containing alumina and zirconia. However, few investigators have reported a sensor structure in which both an oxygen concentration detection cell and an oxygen pump cell are formed on the same surface of a solid electrolyte layer, wherein one of electrodes of each cell is disposed within a common gas diffusion chamber and the other electrode is formed outside the gas diffusion chamber, and wherein the pump cell which utilizes oxygen ions flowing in a direction of the planer surface of the solid electrolyte layer is disposed on a common plane of the alumina substrate). Moreover, few investigators have reported technical problems arising from such a two-cell sensor structure having at least a pair of pump cell electrodes formed on a planer electrolyte layer surface.

SUMMARY OF THE INVENTION

The present invention can solve the above-described problems as well a potential problems, and an object of the present invention is to provide a gas sensor element which assumes a shape advantageous in terms of structural strength, which can be activated quickly and perform accurate measurement with a low consumption of electric power, and which can be manufactured at relatively low cost.

A gas sensor element according to the present invention has at least one of the following major features. Reference numerals inserted herein are only for the purpose of explaining the invention and do not limit the invention to specific drawings.

(1) As shown in FIG. 1, at least an oxygen pump cell (13) and an oxygen detection cell (14) are respectively formed with different solid electrolyte layers (131,141) that are ionically separated by a portion of an insulative ceramic base (11).

(2) Electrodes of the pump cell (13) are coplanerly formed on a common face of the solid electrolyte layer (131) such that oxygen ions flow in a layer-plane direction of the solid electrolyte layer (131), not in a thickness direction thereof normal to the layer plane direction.

(3) An insulative base (11) having a ceramic member preferably covering a heating resistor (12) is integrated with the solid electrolyte layers (131,141).

(4) A diffusion-chamber-forming member (161) is integrated with the insulative base to form a diffusion chamber 16 and a partition wall (162) such that an end of the partition wall (162) extending from the diffusion-chamber-forming member (161) is bonded to a surface of the solid electrolyte layer (131), the surface being located between the electrodes (1321/1322) of the pump cell (13).

(5) One electrode (1421) of the oxygen detection cell (14) is exposed to a gas atmosphere in the diffusion chamber (16), and the other electrode (1422) as an oxygen reference electrode is disposed outside the diffusion chamber (16).

(6) The solid electrolyte layer contains zirconia and alumina, and when the total amount of the zirconia and the alumina is defined as 100% by mass, the alumina content is 10 to 80% by mass, and the alumina has a mean grain size not greater than 1.0 $\mu$m.

(7) A boundary portion within 20 $\mu$m from a plane of junction between the solid electrolyte layer (131) and the partition wall (162) contains no portion in which the amount of substances other than alumina exceeds by 2% by mass or more the amount of substances, other than alumina, of the diffusion-chamber-forming member (161).

(8) The insulative base (11), the heating resistor (12), the solid electrolyte layers (131,132), the electrodes (1321, 1322, 1421, 1422) and the diffusion-chamber-forming member (161) are unitarily integrated through simultaneous firing or cofiring.

(9) A portion of the partition wall within 20 $\mu$m of a plane of junction between the partition wall (162) and the solid electrolyte layer (131) of the oxygen pump cell (13) is defined as a partition wall junction portion, the total amount of alkali metals, alkaline earth metals, and silicon contained in the partition wall junction portion is 2% by mass or less as reduced to their respective oxides, with respect to the entire partition wall junction portion.

(10) A migration prevention conductor (152) for preventing the heating resistor (12) from degradation is provided on the surface of or within the insulative base (11), (as shown in FIG. 5).

The object of the present invention has been achieved by providing, in a first embodiment, a gas sensor element comprises an insulative base including an insulative ceramic member and a heating resistor formed on a surface of or inside the insulative ceramic member; and one or more oxygen pump cells and one or more oxygen detection cells, the cells being joined directly to the insulative base or indirectly to the insulative base via another member and each having a solid electrolyte layer and a pair of electrodes formed on a surface of the solid electrolyte layer, wherein the insulative ceramic member contains alumina as a predominant component; a diffusion chamber is defined by a diffusion-chamber-forming member having a rate-controlling introduction portion for introduction of a gas to be measured; and one of the electrodes of at least one oxygen pump cell and one of the electrodes of at least one oxygen detection cell are disposed on a common wall surface of the diffusion chamber.

At least one oxygen pump cell may be configured such that both the electrodes of the oxygen pump cell are disposed on the same surface of the solid electrolyte layer of the oxygen pump cell, and a partition wall containing alumina as a predominant component is provided between the electrodes such that one end of the partition wall is joined to the surface of the solid electrolyte layer. The diffusion-chamber-forming member may contain alumina as a predominant component. The partition wall may constitute a portion of the diffusion-chamber-forming member. The gas sensor element may be fabricated through simultaneous firing (or rather cofiring). When a portion of the partition wall within 20 $\mu$m of a plane of junction between the partition wall and the solid electrolyte layer of the oxygen pump cell is defined as a partition wall junction portion, the total amount of alkali metals, alkaline earth metals, and silicon contained in the partition wall junction portion is 2% by mass or less as reduced to their respective oxides, with respect to the entire partition wall junction portion.

Further, when a portion of the partition wall excluding the partition wall junction portion is defined as a partition wall remaining portion, the total amount of alkali metals, alkaline earth metals, and silicon contained in the partition wall remaining portion is 1% by mass (i.e., by weight) or less as reduced to their respective oxides, with respect to the entire partition wall remaining portion. The solid electrolyte layer may contain zirconia and alumina, and when the total amount of the zirconia and the alumina is defined as 100% by mass, the alumina content may be 10 to 80% by mass, and the alumina may have a mean grain size not greater than 1.0 $\mu$m. The insulative ceramic member may contain alumina in an amount of 70% by mass or more. Further, the insulative ceramic member may contain alumina in an amount of 99% by mass or more. Moreover, the insulative ceramic member may contain alumina in an amount of not less than 70% by mass but less than 99% by mass; the heating resistor may include a heat generation portion which generates heat upon application of voltage thereto, and a lead portion connected to the heat generation portion and having a width greater than that of the heat generation portion; and a migration prevention conductor may be provided on the surface of or within the insulative base, the migration prevention conductor being maintained at a potential equal to or lower than a potential at the boundary between the heat generation portion and the lead portion.

A second embodiment of the present invention provides a gas sensor element that comprises an insulative base (11); a heating resistor (12) formed within the insulative base (11); a plurality of solid electrolyte layers (131, 141) disposed on one face of the insulative base (11); an oxygen pump cell (13) having a pair of electrodes (1321/1322) disposed on a common surface of one solid electrolyte layer (131); an oxygen detection cell (14) having a pair of electrodes (1421/1422) disposed on a common surface of the other solid electrolyte layer (141); and a diffusion-chamber-forming member (161) having a rate-controlling introduction portion (163) through which a gas to be measured passes and defining a diffusion chamber (16) in cooperation with one electrode (1321) of the oxygen pump cell and one electrode (1421) of the oxygen detection cell, the insulative base, the heating resistor, the solid electrolyte layers, the oxygen pump cell, the oxygen detection cell, and the diffusion-chamber-forming member having been integrated through simultaneous firing, wherein (a) each of the insulative base (11) and the diffusion-chamber-forming member (161) contains alumina as a predominant component;

(b) a partition wall (162), which extends from the diffusion-chamber-forming member (161), is joined to a surface of a solid electrolyte (131) between a pair of electrodes (1321/1322) of the oxygen detection cell; and (c) a boundary portion within 20 $\mu$m of a plane of junction between the solid electrolyte (131) and the partition wall (162) contains no portion in which the amount of substances other than alumina exceeds by 2% by mass or more the amount of substances, other than alumina, of the diffusion-chamber-forming member (163).

The solid electrolytes (131, 132) may contain zirconia ceramic in an amount of 20 to 90% by mass and alumina in an amount of 10 to 80% by mass.

Moreover, the insulative base (11) may contain alumina in an amount of not less than 70% by mass but less than 99% by mass; the heating resistor (12) may include a heat generation portion (121) which generates heat upon application of voltage thereto, and a lead portion (122) connected to the heat generation portion and having a width greater than that of the heat generation portion; and a migration prevention conductor (152) may be provided on the surface of the insulative base (11) or within the insulative base (11), the migration prevention conductor (152) being maintained at a potential equal to or lower than a potential at the boundary between the heat generation portion (121) and the lead portion (122).

A gas sensor according to the present invention is characterized by comprising a gas sensor element having one of the features described above or a combination thereof.

Advantages of the Invention:

The gas sensor element of the present invention can assume a structure in which at least two cells are provided side by side on an insulative base containing alumina as a main component (namely, a structure in which cells are not stacked on one another). Therefore, unlike a gas sensor element having stacked cells, the gas sensor element of the present invention does not require provision of a thin layer for separating diffusion chambers, and therefore can assume a structure that is more stable and advantageous in terms of strength. In particular, the distance between the heating resistor and each solid electrolyte layer can be shortened, to thereby increase transmission speed of heat and shorten a heating time for activating each cell. Therefore, the gas sensor element of the present invention can start its operation quickly. Moreover, since the temperature of the solid electrolyte layers can be controlled quickly, more accurate measurement can be performed. Further, consumption of electric power can be reduced. Moreover, as compared with a gas sensor element having stacked cells, a number of operations for layer stacking and printing required during fabrication of the gas sensor element of the present invention can be reduced, so that the above-described excellent gas sensor element can be fabricated with ease and in a stable manner.

Since a partition wall containing alumina as a predominant component is provided for the pair of electrodes of the oxygen pump cell that requires a large amount of electric power for pumping oxygen, leakage of current between the cell electrodes along the surface of the solid electrolyte can be prevented, whereby a reliable gas sensor element can be obtained.

Since the diffusion-chamber-forming member, which defines at least one wall surface of the diffusion chamber, contains alumina as a predominant component, the cells and the diffusion chamber are disposed between two members each containing alumina as a predominant component; i.e., the diffusion-chamber-forming member and the insulative base containing alumina as a predominant component and including the heating resistor. Accordingly, heat transfer between major portions of the element is greatly enhanced, and, in particular, a constant temperature can be maintained throughout the diffusion chamber. Therefore, the equilibrium of gas components between the electrodes of the oxygen pump cell and the oxygen detection cell disposed within the diffusion chamber can be maintained with ease, whereby more accurate measurement (e.g., measurement of air-fuel ratio) can be performed.

When the partition wall is a portion of the diffusion-chamber-forming member, the structure becomes simpler as compared with the case in which the partition wall is provided independently of the diffusion-chamber-forming member, so that fabrication of the gas sensor element can be simplified, while excellent heat transfer is maintained.

The insulative base whose major portion is formed of an insulative ceramic member containing alumina as a predominant component, the cells whose major portions are formed of solid electrolyte layers, the diffusion-chamber-forming member containing alumina as a predominant component and defining the diffusion chamber, etc., are integrated through simultaneous firing. Therefore, the heating time required for activating the cells can be shortened further, whereby the gas sensor element can start its operation more quickly. Moreover, excellent heat transfer is attained, the temperature of the solid electrolyte layers can be controlled quickly, and more accurate measurement (e.g., measurement of air-fuel ratio) can be performed.

Since the total amount of alkali metals, alkaline earth metals, and silicon contained in the partition wall junction portion is 2% by mass or less as reduced in a predetermined manner, leakage of current between the pair of electrodes of the Ip cell (first Ip cell) can be prevented more effectively, whereby a reliable gas sensor element can be obtained.

Since the total amount of alkali metals, alkaline earth metals, and silicon contained in the partition wall remaining portion is 1% by mass or less as reduced in a predetermined manner, the amount of the above-described components contained in the partition wall junction portion and the solid electrolyte layer junction portion can be maintained at 2% by mass or less without fail.

Since the solid electrolyte layers each contains alumina in a predetermined amount and the alumina has a predetermined grain size, the solid electrolyte layers do not suffer generation of cracks or breakage, which would otherwise occur when the cells are integrated, through firing, with the insulative base whose major portion is formed of an insulative ceramic member containing alumina as a predominant component. Moreover, when the solid electrolyte contains zirconia as a predominant component, its phase transition during use can be prevented effectively, whereby a highly reliable gas sensor can be provided.

Since the insulative ceramic member contains alumina in an amount of 70% by mass, leakage of current within the heating resistor is prevented, the insulation between the cells formed on the insulative base can be made more reliable, and the mechanical strength of the entire gas sensor element can be increased to a sufficient level.

When the insulative ceramic member contains alumina in an amount of 99% by mass or more, current leakage within the heating resistor is prevented more reliably, and the insulation between the cells formed on the insulative base can be made more reliable. In addition, heat generated from the heating resistor can be transmitted to the cells uniformly in a stable manner, and consumption of electric power can be reduced. Also, thinning or breaking of the heating resistor due to migration can be prevented.

Moreover, by virtue of using the gas sensor element of the present invention, the gas sensor of the present invention can achieve the above-described advantages.

Figure 1:
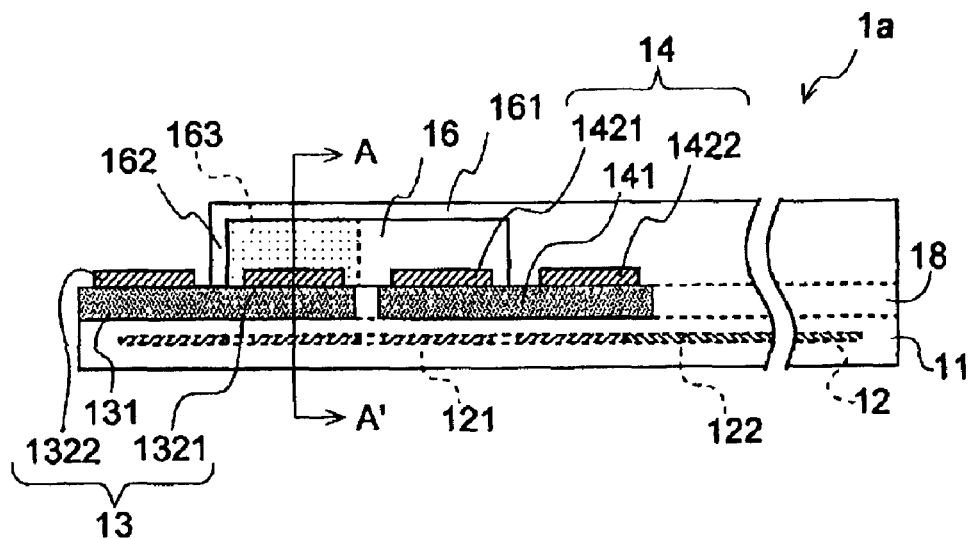
FIG. 1 is a schematic view showing a longitudinal cross section of one example of the gas sensor element of the present invention.

DESCRIPTION OF REFERENCE NUMERALS 1 (1a–1j): gas sensor element, 11: insulative base, 111: green insulative base lower layer, 112: green insulative base upper layer, 12: heating resistor (green heating resistor), 121: heat generation portion, 122: lead portion, 13: Ip cell, 131: solid electrolyte layer for the Ip cell, 132: electrodes for the Ip cell, 1321: negative electrode for the Ip cell, 1322: positive electrode (green positive electrode) for the Ip cell, 13-1: first Ip cell, 131-1: solid electrolyte layer for the first Ip cell, 132-1: electrodes for the first Ip cell, 1321-1: negative electrode for the first Ip cell, 1322-1: positive electrode for the first Ip cell, 13-2: second Ip cell, 131-2: solid electrolyte layer for the second Ip cell, 132-2: electrodes for the second Ip cell, 1321-2: negative electrode for the second Ip cell, 1322-2: positive electrode for the second Ip cell, 133: solid electrolyte layer junction portion, 1311: green Ip cell solid electrolyte layer lower, 1312: green Ip cell solid electrolyte layer upper, 134: green common negative electrode for the Ip and Vs cell, 14: Vs cell, 141: solid electrolyte layer for the Vs cell, 142: electrodes for the Vs cell, 1421: negative electrode for the Vs cell, 1422: positive electrode (green positive electrode) for the Vs cell, 1411: green Vs cell solid electrolyte layer lower, 1412: green Vs cell solid electrolyte layer upper, 151: auxiliary electrode, 152: migration prevention conductor, 153: electrode seal portion, 154: green lead electrodes for the heating resistor, 155: green lead electrodes for the Ip and Vs cells, 16: diffusion chamber, 16-1: first diffusion chamber section, 16-2: second diffusion chamber section, 161: diffusion-chamber-forming member (green diffusion-chamber-forming member), 162: partition wall (green partition wall), 1621: partition wall junction portion, 163: rate-controlling introduction portion (green rate-controlling introduction portion), 164: nitrogen-oxide rate-controlling portion, 165: to-be-burned member for the diffusion chamber, 166: green fourth insulating layer, 17: reference gas introduction passage, 18: additional member, 181: green first insulating layer, 182: green second insulating layer, 183: green third insulating layer, 2: gas sensor, 21: metallic shell, 211: attachment threaded portion, 22: double protector, 23: outer sleeve, 24: element holder, 25: buffer material, 26: sleeve, 27: lead frame, 28: lead wire, 29: separator, 30: grommet

DETAILED DESCRIPTION OF THE PREFERRED EMBODIMENT

The present invention will next be described in detail with reference to the drawings; however, the present invention should not be construed as being limited thereto The gas sensor element according to the present invention (hereinafter also referred to as an "element") essentially comprises the following four members: an insulative base, an oxygen pump cell, an oxygen detection cell, and a diffusion chamber.

The above-described "insulative base" includes an insulative ceramic member and a heating resistor. The insulative base, which serves as a substrate supporting the below-mentioned oxygen pump cell and oxygen detection cell, electrically insulates the cells and serves as a heater for operating the cells.

The above-described "insulative ceramic member" constitutes a major portion of the insulative base and contains alumina as a predominant component. The ceramic member, containing alumina as a predominant component, exhibits more excellent high-temperature insulative properties as compared with zirconia material, which is widely employed as an insulative member of conventional heater elements. For example, at 800° C. the member can provide an electric resistance between a heating resistor and a cell of 1 MΩ or more, preferably 10 MΩ or more. The insulative ceramic member, containing alumina as a predominant component, can enhance its thermal conductivity, which is advantageous in heating each cell.

Preferably, the insulative ceramic member contains alumina in an amount of 70% by mass or more (the entirety of the insulative ceramic member being 100% by mass), more preferably 90 to 100% by mass, still more preferably 95 to 100% by mass. When the amount is less than 70% by mass, properties such as insulative properties, heat resistance, and thermal impact resistance may be difficult to attain simultaneously.

The balance (i.e., components other than alumina) may contain the same component as the predominant component of another member (e.g., zirconia, which is the predominant component of each cell) to be stacked directly on the insulative ceramic member in an amount of 20% by mass or less. The amount is preferably 0.5 to 10% by mass, more preferably 1 to 5% by mass. Incorporation of the above component prevents excessive growth of alumina grains during sintering, thereby reducing the difference in thermal expansion coefficient between the insulative ceramic member and another member to be stacked directly thereon.

Preferably, the insulative ceramic member contains substantially no alkali metals (particularly, Li, Na, and K) or alkaline earth metals (particularly, Mg, Ca, and Ba). Excess amounts of these metals are not preferred, since, as described below, migration of ionized alkali metal ions or alkaline earth ions produced during operation of the heating resistor may break the heating resistor. Preferably, the amount of alkali metals and alkaline earth metals contained in the insulative ceramic member is reduced to 1% by mass or less, as reduced to their respective oxides, (the entirety of the insulative ceramic member being 100% by mass).

The insulative base can be produced by stacking single-layer green sheets of an insulative ceramic to thereby form a green laminate, and firing the green laminate (note that a green heating resistor to become a heating resistor is separately formed on a surface of or within the laminate). The single-layer green sheets may be formed of materials having different compositional proportions. This enables formation of a structure in which the same component as the predominant component of another portion to be formed directly on the insulative base (e.g., zirconia material which constitutes a solid electrolyte of each cell) is incorporated into the insulative base such that the proportion of the incorporated component is varied in a graded manner from the interior of the green laminate to the surface thereof. Through such a graded composition, ease of simultaneous sintering of the insulative base and other portions to be formed directly thereon can be enhanced.

The aforementioned "heating resistor" generates heat when electricity is supplied thereto. The heating resistor is provided on a surface of or within the insulative ceramic member. In general, the surface or inside of the insulative ceramic member serves as the surface or the inside of the insulative base. No particular limitation is imposed on the shape of the heating resistor, and the resistor can be formed into any conventional shape. Preferably, the resistor has a shape which allows effective and sufficient heating of an oxygen pump cell(s) and an oxygen detection cell(s). For example, a heating resistor (12) shown in FIG. 25 has a zigzag shape such that the pattern density thereof is higher directly under each cell. Alternatively, the resistor may be formed into another shape such that the resistor extends along the periphery of a solid electrolyte layer of each cell (e.g., a U-like shape). No particular limitation is imposed on the dimensions of the heating resistor, and the dimensions may correspond to those of each cell.

No particular limitation is imposed on the material for forming the heating resistor, and examples of the material include noble metals, tungsten, molybdenum, and rhenium. When the heating resistor predominantly comprises platinum, the resistor may contain rhodium in an amount of approximately 5 to 20% by mass based on the entirety of the resistor. Such a rhodium-containing heating resistor is preferred, since the resistor is easy to fire together with solid electrolyte layers during a production process. Such a resistor has a reduced temperature coefficient of resistance and can start its operation quickly.

The heating resistor can be produced by mixing materials such as a raw material powder containing the above materials or raw material organometallic compounds (liquid), a binder, a plasticizer, a dispersant, and a solvent, to thereby produce a slurry or paste; forming a layer of the slurry or paste (e.g., through printing); drying the layer to thereby yield a green heating resistor; and firing the green heating resistor.

The insulative base according to the present invention may contain, in addition to the insulative ceramic member and the heating resistor, other members, such as a migration prevention conductor and a ceramic member for supporting the migration prevention conductor.

Among them, the aforementioned "migration prevention conductor" is a conductor provided on a surface (e.g., 152 in FIG. 4) of or within (e.g., 152 in FIG. 5) an insulative ceramic member (generally on a surface or within the insulative base). The migration prevention conductor is maintained at a potential equal to or lower than a potential at the boundary between a heat generation portion and a lead portion of the heating resistor. When provided within the insulative ceramic member, the migration prevention conductor may be provided on an imaginary plane which is identical to or different from the plane of the heating resistor.

Through provision of the migration prevention conductor, ionized species contained in the insulative ceramic member such as ionized alkali metals and ionized alkaline earth metals can be drawn to the migration prevention conductor, so that the ionized species hardly migrate to the heating resistor. Thus, thinning and breakage of the heating resistor can be prevented.

The migration prevention conductor may be provided alone or may be branched from a portion of the heating resistor. When the migration prevention conductor is provided alone, the conductor is grounded (such that the potential of the conductor decreases to, for example, 1 V or lower), and no electricity is supplied to the conductor. Thus, the conductor serves as a migration prevention conductor. When the migration prevention conductor is provided as a portion of the heating resistor, a conductor is branched from the lower-potential-side end of the heating resistor and electrically isolated from the higher-potential side of the heating resistor. Thus, the conductor serves as a migration prevention conductor.

No particular limitation is imposed on the shape of the migration prevention conductor, and the conductor may be of a straight-line pattern or a zigzag pattern. Alternatively, the migration prevention conductor may assume the same shape as that of the heating resistor (however, one end of the conductor is not connected to the heating resistor or other constituent elements); e.g., the shape of a heating resistor (12) shown in FIG. 25 or a generally U-shaped resistor. No particular limitation is imposed on the material for forming the migration prevention conductor, and the conductor is generally formed of a material similar to that for forming a heating resistor.

The migration prevention conductor can be provided regardless of the composition of the insulative ceramic member. Specifically, even when the insulative ceramic member contains alumina in an amount of 99% by mass or more (the entirety of the insulative ceramic member being 100% by mass), the migration prevention conductor may be provided. Particularly, the conductor is effective when the alumina content is not less than 70% by mass but less than 99% by mass. Furthermore, the conductor is more effective when the total amount of alkali metals and alkaline earth metals, as reduced to their oxides, is 1% by mass or more, preferably 3% by mass or more, more preferably 4% by mass or more (generally 10% by mass or less). As used herein, the expression "as reduced to their oxides" means a calculation performed on the basis of $M_2O$ when M is an alkali metal and MO when M is an alkaline earth metal.

The aforementioned "oxygen pump cell" (hereinafter also referred to as an Ip cell) pumps oxygen into and out of the diffusion chamber and enables detection of current required for pumping in and out.

The aforementioned "oxygen detection cell" (hereinafter also referred to as a Vs cell) detects oxygen concentration in the diffusion chamber and outputs the detected oxygen concentration in the form of an electric potential difference.

These Ip and Vs cells may be arranged in parallel or in series along the longitudinal direction of the element. The manner of arrangement may be appropriately determined in accordance with, for example, the site in which a sensor element is accommodated or the site to which a sensor containing the sensor element is attached. Among the above-described manners of arrangement, a serial arrangement is preferred, since larger solid electrolyte layers can be readily formed.

Each of the Ip cell and the Vs cell contains a solid electrolyte layer, and a pair of electrodes formed on the solid electrolyte layer. However, the solid electrolyte layers of the Ip and Vs cells may be consolidated, and/or the electrodes of the Ip and Vs cells may be consolidated, so long as the functions of the Ip cell and the Vs cell can be provided. In other words, the Ip cell and the Vs cell may share a single solid electrolyte layer. The same is applicable to the electrodes. However, a solid electrolyte layer forming an Ip cell and that forming a Vs cell are preferably separated, and these solid electrolyte layers are isolated from each other. Such isolation assures electric insulation between cells.

The sensor element according to the present invention may contain one or more Ip cells and one or more Vs cells. For example, the sensor element may contain one Ip cell and one Vs cell. Such an element can be used as a full-range air-fuel ratio sensor. Alternatively, the sensor element may contain two Ip cells and one Vs cell. Such an element can be used as a nitrogen oxide sensor element or a flammable gas (e.g., carbon monoxide or hydrocarbon gas) sensor element. Alternatively, the sensor element may contain three Ip cells and two Vs cells. Such an element can be used as a compound gas sensor element which allows sensing of a plurality of gas species including oxygen, nitrogen oxides, and flammable gas (e.g., simultaneous sensing of carbon monoxide and nitrogen oxides). By further increasing the number of these cells, a gas sensor which allows simultaneous sensing of two or more gas species including oxygen, nitrogen oxides, flammable gas, and steam (vapor) can be produced.

The aforementioned "solid electrolyte layer" forms an Ip cell and a Vs cell. No particular limitation is imposed on the solid electrolyte material for forming the solid electrolyte layer, and a variety of solid electrolyte materials can be employed. Examples of the solid electrolyte materials include zirconia materials and Perovskite materials (e.g., $LaGaO_3$). Of these, zirconia materials are preferred. Specifically, zirconia species stabilized by at least one element selected from among Y, Mg, Ca, Sc, and rare earth elements (including stabilized zirconia and partially stabilized zirconia) are more preferred. Y-stabilized zirconia (hereinafter referred simply to as "YSZ") is particularly preferred, since YSZ exhibits well-balanced oxygen ion conductivity and mechanical strength. Preferably, the YSZ contains Y (as reduced to $Y_2O_3$) in an amount of 2 to 9 mol %, more preferably 4 to 9 mol % (the total amount of zirconia species contained in the solid electrolyte layer being 100 mol %). When the amount of Y falls within the above-described range, phase transition of zirconia hardly occurs even when temperature increases and decreases during a firing process and a cooling-heating cycle. The above zirconia materials may contain hafnium.

Preferably, the solid electrolyte layer contains alumina, which is a predominant component of the insulative ceramic member forming the insulative base. Through incorporation of alumina, the difference in thermal expansion coefficient between the solid electrolyte layer and the insulative ceramic member can be reduced.

Preferably, the solid electrolyte layer contains alumina in an amount of 10 to 80% by mass, more preferably 15 to 60% by mass, particularly preferably 15 to 50% by mass. Preferably, the alumina contained in the solid electrolyte layer has a mean grain size of 1.0 μm or less, more preferably 0.05 to 0.8 μm, particularly preferably 0.1 to 0.6 μm. When the alumina content and the mean grain size of alumina fall within the above ranges, the difference in thermal expansion coefficient is effectively reduced. Particularly when the solid electrolyte layer is simultaneously fired with the insulative base, cracking and breakage of the solid electrolyte layer can be prevented.

The alumina content and the mean grain size may be selected in combination so long as these two fall within the respective ranges described above. For example, preferably, the alumina content is 10 to 80% by mass and the mean grain size of alumina is 1.0 μm or less, more preferably 15 to 60% by mass and 0.05 to 0.8 μm, particularly preferably 15 to 50% by mass and 0.1 to 0.6 μm.

Through incorporation of alumina, the mean grain size of zirconia can be decreased to 2.5 μm or less (preferably 0.1 to 2.3 μm, more preferably 0.3 to 2.0 μm). In addition, the maximum grain size of zirconia can be decreased to 5 μm or less (preferably 4.2 μm or less, more preferably 3.5 μm or less, generally at least 0.5 μm). Employment of YSZ enables considerably effective suppression of phase transition caused by temperature changes during a firing process or a cooling-heating cycle in an environment in which the gas sensor is used. Even when phase transition occurs in a portion of YSZ, stress is readily dispersed, thereby preventing crack generation.

Zirconia grains contained in the solid electrolyte layer may comprise particles of tetragonal phase (hereinafter "T phase"), those of monoclinic phase (hereinafter "M phase"), and those of cubic phase (hereinafter "C phase"). Particularly, the mean grain size of, among other grains, T-phase grains can be decreased to 2.5 μm or less (preferably 0.1 to 2.3 μm, more preferably 0.3 to 2.0 μm). The T phase is prone to cause phase transition to M phase, particularly at about 200° C. This phase transition is known to be accelerated by moisture and involves a change in volume. Thus, by suppressing the mean grain size of the T-phase grains to 2.5 μm or less, phase transition of zirconia caused by temperature changes during a firing process and a cooling-heating cycle can be remarkably suppressed.

The alumina content and the zirconia content can be obtained through generally employed chemical analysis or through image analysis of electron microscopic photographs. Specifically, a back-scattered electron image (hereinafter referred simply to as "BEI") is photographed under an electron microscope at a magnification of ×5,000, and the photograph is converted to the corresponding electronic information by means of, for example, a scanner. The electronic information thus obtained is analyzed by means of an image analyzer (e.g., Luzex FS, product of Nireko Corporation), to thereby calculate percent area of grains of a specific composition. The corresponding approximate theoretical percent volume derived from the percent area can serve as the alumina content or zirconia content.

The mean grain size of alumina is determined by use of a photograph of a surface of a solid electrolyte layer obtained under an electron microscope at a magnification of ×5,000 (hereinafter referred to as a SEM photograph). In the SEM photograph, the maximum grain size of alumina grains is regarded as the alumina grain size, and the mean grain size calculated from all alumina grains included in a unit square (5 cm×5 cm) serves as a primary mean grain size. In a similar manner, primary mean grain sizes are determined from five SEM photographs obtained at different observation areas (surface) on the same solid electrolyte layer, and the thus-obtained primary mean grain sizes are averaged, to thereby obtain a secondary mean grain size, which serves as the mean grain size used in relation to the present invention. The mean grain size of zirconia can be determined in the same manner. However, the mean grain size of T-phase grains can be obtained by use of BEI, and the grains can be distinguished from grains of other phases.

The aforementioned "electrodes" are conductors provided on the solid electrolyte layers of the Ip and Vs cells. The electrodes are provided such that each of the cells can use at least one pair of electrodes. Therefore, two electrodes may be provided for each of the cells so as to enable each cell to use a pair of electrodes. Alternatively, one electrode is provided for each of the cells and a common electrode is provided for the cells so as to enable each cell to use a pair of electrodes. Examples of the case in which such a common electrode is provided include the case of a two-cell-type element in which the negative electrode of the Ip cell and the negative electrode of the Vs cell are consolidated into a single common negative electrode and the case of a multi-cell-type element having three or more cells in which the negative electrode of the first Ip cell and the negative electrode of the Vs cell are consolidated into a single common negative electrode.

The electrodes are formed on the solid electrolyte layers. One electrode of at least one Ip cell and one electrode of at least one Vs cell are disposed on a common wall surface of the diffusion chamber. Specifically, in the example shown in FIG. 1, a negative electrode (1321) for an Ip cell and a negative electrode (1421) for a Vs cell are disposed on a common wall surface of the diffusion chamber (16). In the example shown in FIG. 6, a negative electrode (1321-1) for an Ip cell and a negative electrode (1421) for a Vs cell are disposed on a common wall surface of the diffusion chamber (16).

Excepting the above, no restriction is imposed on the positional relation between the electrodes. Therefore, the remaining electrodes may be disposed freely. In the example shown in FIG. 6, a positive electrode (1422) for the Vs cell is formed between the diffusion chamber (16) and a solid electrolyte layer (141) for the Vs cell. In the example shown in FIG. 9, a positive electrode (1322-2) for a second Ip cell is formed between an insulative base (11) and a solid electrolyte layer (131-2) for the second Ip cell. However, in general, the electrodes are formed of a porous material, which tends to have a lower thermal conductivity as compared with a dense material. Therefore, from the viewpoint of quick transfer of heat from the heating resistor to the solid electrolyte layers, preferably, the electrodes are not disposed between the insulative base and the solid electrolyte layers.

The above-described "disposed on a common inner wall surface" includes not only the case in which the relevant electrodes are formed on a common inner wall surface consisting of a single flat surface, but also the case in which the common inner wall surface has raised and depressed portions; i.e., consists of a plurality of flat surfaces and the electrodes are formed on the plurality of surfaces.

In general, at least one of the electrodes of the Vs cell must function as a reference electrode which serves as a reference for oxygen concentration. Further, when two or more Ip cells are provided, one electrode must function as a similar reference electrode in some cases. Two schemes; i.e., a self-reference generation scheme and a reference gas introduction scheme, can be employed in order to cause such an electrode to function as a reference electrode. In the self-reference generation scheme, an electrode is held airtight by means of a dense ceramic member, and, through utilization of oxygen pumping action of a cell, an oxygen atmosphere of constant pressure is created within the space between the electrode and the dense ceramic material or within pores of a porous material of the electrode (e.g., an electrode 1422 in FIG. 1). In the reference gas introduction scheme, a passage (e.g., a passage 17 in FIG. 4, and a passage 17 in FIG. 10) is formed in the element in order to introduce a reference gas serving as a reference of oxygen concentration (e.g., atmospheric air or inert gas) to a relevant electrode such that the electrode is exposed to the reference gas. The element according to the present invention may employ either of the above-described schemes. However, the self-reference generation scheme is preferably employed in the case in which the element is small, in the case in which heat from the heating resistor must be transmitted uniformly, or in the case in which the mechanical strength of the entire element must be increased.

Each of the Ip and the Vs cells may have an additional electrode(s) other than the pair of electrodes. Examples of such an additional electrode include an auxiliary electrode for increasing electrical conduction between the electrodes (e.g., an auxiliary electrode 151 in FIGS. 5, 8, etc.) and a resistance reference electrode used for measurement of resistance of a solid electrolyte layer. When the auxiliary electrode is provided for the Ip cell, which desirably has a low resistance, the resistance of the Ip cell can be reduced efficiently. When the resistance reference electrode is provided for a solid electrolyte layer, data regarding the resistance of the solid electrolyte layer can be fed, as a feedback signal, to a controller, which controls the quantity of electricity supplied to the heating resistor on the basis of the data, to thereby accurately control the temperature of the solid electrolyte layer at all times. Therefore, the conductivity of the solid electrolyte layer can be maintained at a target level at all times.

No particular limitation is imposed on the size of the electrodes of each cell. However, each of the electrodes of the Ip cell (in a multi-cell-type element, a first Ip cell disposed at a most upstream position within the diffusion chamber) preferably has an area of 1 to 20 mm$^2$ (more preferably, 6 to 10 mm$^2$, still more preferably 7 to 9 mm$^2$). When the area is less than 1 mm$^2$, the Ip cell may encounter difficulty in providing sufficient pumping action. By contrast, although an area in excess of 20 mm$^2$ is advantageous in terms of pumping efficiency, such an area is not preferable, in view of an excessive increase in size of the element. Each of the electrodes of the Vs cell preferably has an area of 1 to 15 mm$^2$. When the area is less than 1 mm$^2$, the Vs cell may fail to accurately measure oxygen concentration. By contrast, although an area in excess of 15 mm$^2$ is advantageous in terms of efficiency in measurement of oxygen concentration, such an area is not preferable, in view of an excessive increase in size of the element.

Although each of the electrodes preferably has the above-described area, its length as measured along the width direction of the element is preferably 1 to 5 mm (more preferably 2 to 4 mm, still more preferably 2.5 to 3.5 mm) in order to improve operation efficiency of each electrode and to reduce the size of the element. When the length becomes less than 1 mm, the operation efficiency of each electrode tends to decrease. By contrast, when the length exceeds 5 mm, the element becomes large, which is not preferable.

In many cases, a larger current flows through the Ip cell as compared with the Vs cell. Therefore, the electrodes of the Ip cell are preferably insulated from each other in a more reliable manner. Accordingly, the gap between the electrodes of the Ip cell is preferably 0.01 to 3 mm (more preferably 0.05 to 2 mm, still more preferably 0.07 to 1.5 mm). When the gap becomes less than 0.01 mm, the insulation between the electrodes of the Ip cell may become insufficient. By contrast, when the gap exceeds 3 mm, the element becomes excessively large, which is not preferable.

No particular limitation is imposed on the material of the electrodes, and various types of conductive materials may be used. A selected conductive material preferably has an electrical resistivity of not greater than $10^{-2}$ Ω·cm (Ω·cm is a unit used for representing a resistance of a sample per 1×1×1 cm$^3$). Examples of such a conductive material include noble metal species, transition metal species, and alloys each containing two or more species selected from these metal species. Of these, a conductive material containing a platinum group metal as a predominant component is preferable. Electrodes containing a platinum group metal as a predominant component is excellent in terms of heat resistance and corrosion resistance, and can establish close contact with the corresponding solid electrolyte layer. Each of the electrodes may contain one of major components of a solid electrolyte layer to which the electrode is joined, in an amount of 20% by mass or less (the entirety of one electrode being regarded as 100% by mass). This further improves the degree of closeness of contact with the corresponding solid electrolyte layer.

The above-described "diffusion chamber" is a portion into which a gas to be measured is introduced via a rate-controlling introduction portion with its flow rate controlled and in which the introduced gas is diffused. The diffusion chamber is defined by a diffusion-chamber-forming member. In other words, the diffusion chamber is a space partitioned in such a manner that the space (i.e., the interior of the diffusion chamber) is isolated from the atmosphere outside the element, except at a position of a rate-controlling introduction portion to be described later.

The diffusion chamber may be formed by a single chamber, two or more chambers communicating with one another, or a communication passage only. Examples of the diffusion chamber formed by a single chamber include a diffusion chamber formed by a rectangular parallelepipedic or cubic chamber (e.g., the chamber 16 in FIG. 1) and a diffusion chamber formed by a chamber, a portion of which is reduced in volume. Examples of the diffusion chamber formed by two or more chambers include a diffusion chamber having two chambers (e.g., chambers 16-1 and 16-2 in FIG. 6 and chambers 16-1 and 16-2 in FIG. 11) which communicate with each other via a passage having a cross section smaller than those of the chambers (e.g., a passage 164 in FIG. 7 and a passage 164 in FIG. 11), and a diffusion chamber having two chambers (e.g., chambers 16-1 and 16-2 in FIG. 13) which communicate with each other via a rate-controlling portion capable of controlling the diffusion rate of a gas (e.g., a passage 164 in FIG. 13). Examples of the diffusion chamber formed by only a communication passage include a diffusion chamber formed by a meandering passage having a substantially constant cross section. Notably, when the diffusion chamber is formed by a communication passage only and the diffusion rate of a gas must be changed within the diffusion chamber, the diffusion rate can be adjusted through adjustment of the length of the passage. Notably, the above-described rate-controlling portion provided within the diffusion chamber is the same as the rate-controlling introduction portion to be described later, except that a gas whose diffusion rate is controlled is a gas within the diffusion chamber which may differ from a gas to be measured present outside the element. Therefore, the configuration of the rate-controlling introduction portion can be applied to the rate-controlling portion without any modification.

When an element having two Ip cells and a single Vs cell is to function as a nitrogen oxide sensor element, the element preferably operates such that oxygen contained in a gas under measurement introduced into the diffusion chamber (including oxygen dissociated from a portion of nitrogen oxides) is pumped out by means of the first Ip cell in order to reduce the oxygen concentration in the diffusion chamber; simultaneously or subsequently, the oxygen concentration of the gas under measurement having a reduced oxygen content is measured by means of the Vs cell; and after measurement of oxygen concentration, the concentration of nitrogen oxides in the gas under measurement is measured by means of the second Ip cell. Therefore, the diffusion chamber preferably assumes a shape which enables the gas under measurement to diffuse to the first Ip cell, the Vs cell, and the second Ip cell, in this sequence. For example, the diffusion chamber may be divided into a first diffusion chamber section in which pumping by the first Ip cell is effected, a second diffusion chamber section in which measurement by the Vs cell is effected, and a third diffusion chamber section in which the concentration of nitrogen oxides is measured by the second Ip cell, these sections being mutually connected by means of passages. Alternatively, the diffusion chamber may be formed by a single meandering passage which enables sequential performance of the above-described operations.

The diffusion chamber may be configured such that its interior is completely hollow or completely filled, or that a portion of the interior is hollow and the remaining portion is not hollow. An example diffusion chamber which is not hollow but enables diffusion of the gas under measurement is a diffusion chamber formed by a continuous-pore-type porous material. When the diffusion chamber is formed by a continuous-pore-type porous material and the diffusion rate of a gas must be changed within the diffusion chamber, the diffusion rate can be adjusted through adjustment of the porosity. For example, when a selected portion of the diffusion chamber is formed by use of a continuous-pore-type porous material having a lower porosity, while the remaining portion is formed by use of a continuous-pore-type porous material having a higher porosity, the selected portion can reduce the diffusion rate of a gas to a greater extent.

The above-described "rate-controlling introduction portion" is a portion through which a gas to be measured is introduced into the diffusion chamber. This rate-controlling introduction portion is provided in a diffusion-chamber-forming member to be described later. No limitation is imposed on the configuration of the rate-controlling introduction portion. For example, the rate-controlling introduction portion may assume a configuration in which a continuous-pore-type porous material is disposed between the diffusion chamber and an atmosphere from which a gas to be measured is to be introduced, and the porous material has a porosity capable of controlling the flow rate of the gas, or a configuration in which a slit or a small hole is provided between the diffusion chamber and an atmosphere from which a gas to be measured is to be introduced. The term "rate-controlling" means adjusting the flow rate of a gas to be measured in such a manner that the gas is introduced into the diffusion chamber at a substantially constant rate irrespective of the flow rate of the gas outside the gas sensor element.

The above-described "diffusion-chamber-forming member" refers to a member which defines and forms the diffusion chamber. This diffusion-chamber-forming member can physically isolate the atmosphere within the diffusion chamber from the outside atmosphere, except at the rate-controlling introduction portion. In general, the diffusion-chamber-forming member is formed of a dense ceramic material. No limitation is imposed on the ceramic material that constitutes the diffusion-chamber-forming member, except the rate-controlling introduction portion, and the ceramic material may be an alumina-containing material or a zirconia-containing material. However, an alumina-containing material; i.e., a ceramic material containing alumina as a predominant component, is preferred, because when the ceramic material contains alumina as a predominant component, the ceramic material has sufficiently high heat resistance and mechanical strength, and has considerably high heat conductivity.

A gas must be maintained at a substantially constant temperature between a point at which the gas comes into contact with the Ip cell electrode and a point at which the gas comes into contact with the Vs cell electrode disposed within the diffusion chamber. When the concentration of oxygen contained in exhaust gas of an automobile is measured, in general, at least carbon monoxide, carbon dioxide, hydrogen, oxygen, and water vapor are introduced into the diffusion chamber. These gases are in a mutual equilibrium state, which is greatly affected by temperature. For example, in response to a temperature increase, the equilibrium state shifts toward a direction to reduce the oxygen content. Therefore, if temperature cannot be maintained constant throughout the diffusion chamber, the concentration of oxygen, which may be an object to be measured or a reference for measurement, changes while the gas moves from the Ip cell to the Vs cell, possibly rendering measurement operation unstable.

The element according to the present invention assumes a structure in which at least one Ip cell and at least one Vs cell are disposed side by side within the same chamber, or rather at least one of the electrodes of the Ip cell and of Vs cell are exposed side by side in the atmosphere of the common chamber. However, maintaining the same temperature between the cells by means of temperature control of the heating resistor becomes difficult, because the chamber has to be made thinly elongated (because the pumping capacity of the Ip cell is limited), and because the position of the Ip cell is different from that of the Vs cell. In such a case, through employment of a diffusion-chamber-forming member made of alumina, a state in which a temperature variation is desired to be smallest between the IP and Vs cells in the diffusion chamber can be quickly established. This is because the alumina has a higher thermal conductivity than other chemically stable insulators and is therefore capable of quick suppression of the temperature variation between the cells by transmitting a thermal energy from one place to the other. In other words, the element is uniformly heated and maintains a constant temperature throughout the diffusion chamber.

In order to obtain further enhanced uniform heating, the inner wall surface of the diffusion chamber formed by the diffusion-chamber-forming member preferably has as large an area as possible. In a preferred embodiment of the element, at least an inner wall surface of the diffusion chamber opposite the common inner wall surface on which two predetermined electrodes are disposed is formed by the diffusion-chamber-forming member comprised of alumina (see FIG. 1, FIGS. 4 to 6, and FIGS. 8 to 11). In other words, the diffusion chamber is covered with the diffusion-chamber-forming member. The inner wall surface has the largest area among the inner wall surfaces that constitute the diffusion chamber. Therefore, a particularly excellent uniform heating effect can be attained. In the elements shown in FIGS. 12 and 13, since the second Ip cell is disposed above the Vs cell, at a portion corresponding to the second Ip cell, the inner wall surface of the diffusion chamber opposite the common inner wall surface is not formed by the diffusion-chamber-forming member. However, since the diffusion-chamber-forming member is provided to cover the second Ip cell as well, an excellent, uniform heating effect can be attained in a similar manner.

The diffusion-chamber-forming member preferably contains alumina in an amount of 70% by mass or more (more preferably 95 to 100% by mass, still more preferably 99 to 100% by mass), where the amount of the entire diffusion-chamber-forming member is defined as 100% by mass. When alumina is contained in an amount of 70% by mass or more, the diffusion-chamber-forming member can exhibit sufficiently high mechanical strength and an excellent, uniform heating effect.

The above-described "partition wall" is used in the case in which negative and positive electrodes of the Ip cell are formed on a common surface of a solid electrolyte layer such that one of the electrodes is disposed within the diffusion chamber. The partition wall is a member which contains alumina as a predominant component, is disposed between the electrodes, and is formed in contact with the surface of the solid electrolyte layer of the Ip cell. The partition wall can prevent leakage of current between the negative and positive electrodes of the Ip cell.

Since a larger current flows through the Ip cell as compared with the Vs cell, an important consideration is to provide a sufficiently high degree of insulation between the electrodes of the Ip cell within the element. In particular, in the element according to the present invention, the electrodes of the Ip cell are difficult to dispose such that one electrode exposed to the atmosphere outside the element is formed on one surface of a solid electrolyte layer and the other electrode disposed within the diffusion chamber is formed on a different surface of the solid electrolyte layer; and therefore, the electrodes of the Ip cell are typically disposed on a common surface of the solid electrolyte layer. Accordingly, a sufficiently high degree of insulation must be provided between the electrodes. Although insulation can be provided through provision of a sufficiently large gap between the electrodes, in this case, the element becomes longer and larger. By contrast, through provision of the partition wall, a sufficiently high degree of insulation can be provided, while a small size of the element is maintained.

Notably, the small-sized element has a length of not greater than 60 mm (preferably not greater than 55 mm, particularly preferably not greater than 50 mm, but generally not less than 30 mm), a width of not greater than 6 mm (preferably not greater than 5 mm, particularly preferably not greater than 4.5 mm, but generally not less than 3 mm), and a thickness of not greater than 3 mm (preferably not greater than 2.5 mm, particularly preferably not greater than 2 mm, but generally not less than 1 mm).

Although the partition wall may be a member separate from the diffusion-chamber-forming member, the partition wall is preferably a portion of the diffusion-chamber-forming member. No particular limitation is imposed on the configuration of the partition wall, so long as the partition wall can provide a sufficient degree of isolation between the predetermined electrodes. Therefore, the above-described rate-controlling introduction portion formed of a continuous-pore-type porous material may be used as a partition wall. Moreover, no particular limitation is imposed on the material of the partition wall, so long as the material of the partition wall contains alumina as a predominant component. The partition wall preferably contains alumina in an amount of 70% by mass or more (more preferably 95 to 100% by mass, still more preferably 99 to 100% by mass). Thus, the partition wall can have a sufficiently high insulation performance and mechanical strength in a well-balanced manner. When the partition wall is a portion of the diffusion-chamber-forming member, the diffusion-chamber-forming member can have excellent thermal conductivity. Likewise, the insulative ceramic member, the insulative base and the diffusion-chamber-forming-member containing alumina as predominant component preferably contains alumina in an amount of 70% by mass or more (more preferably 95 to 100% by mass, still more preferably 99 to 100% by mass).

Moreover, in the vicinity of the plane of junction between the partition wall and the solid electrolyte layer, the amount of alkali metals, alkaline earth metals, and silicon contained in the partition wall is preferably reduced to the smallest possible extent. In the case in which the partition wall containing alumina as a predominant component and a solid electrolyte layer containing zirconia or the like as a predominant component are formed through simultaneous firing of materials of the partition wall and the solid electrolyte layer, a glass component easily precipitates at the boundary between the partition wall and the solid electrolyte layer due to eutectic crystallization, if an alkali metal, an alkaline earth metal, or silicon is present. Since the precipitated glass component causes leakage of current at high temperature, a state is preferably established in which precipitation of a glass component is hardly observed in the partition wall in the vicinity of the plane of junction.

Figure 3:
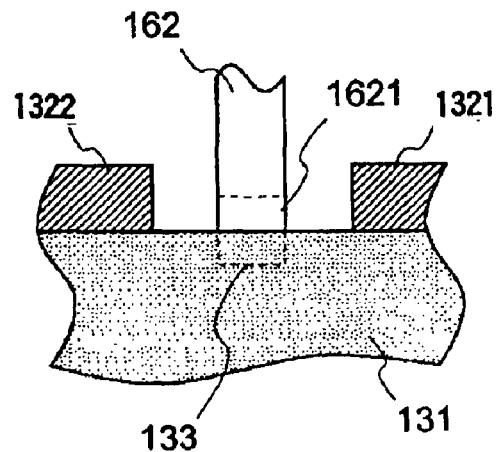
FIG. 3 is an explanatory view for explaining the partition wall junction portion and the solid electrolyte layer junction portion.

Such a state in which precipitation of a glass component is hardly observed is defined as follows. When a portion of the partition wall within 20 $\mu$m of a plane of junction between the partition wall and the solid electrolyte layer of the Ip cell is defined as a partition wall junction portion (1621 in FIG. 3), the total amount of alkali metals, alkaline earth metals, and silicon contained in the partition wall junction portion is 2% by mass or less (more preferably 0 to 1.5% by mass, still more preferably 0 to 1.0% by mass) as reduced to their respective oxides, with respect to the entire partition wall junction portion.

Further, in order to reduce to a smallest possible extent the total amount of alkali metals, alkaline earth metals, and silicon contained in the partition wall junction portion, preferably, the following condition is satisfied. When a portion of the partition wall excluding the partition wall junction portion is defined as a partition wall remaining portion, the total amount of alkali metals, alkaline earth metals, and silicon contained in the partition wall remaining portion is 1% by mass or less as reduced to their oxides (more preferably 0 to 0.7% by mass, still more preferably 0 to 0.5% by mass), with respect to the entire partition wall remaining portion.

Although influence on the insulation of the electrodes may be smaller than that caused by the predetermined components contained in the partition wall junction portion, some components contained in the solid electrolyte layer may affect the insulation of the electrodes if the solid electrolyte layer contains, as a predominant component, zirconia completely or partially stabilized by yttria.

Therefore, in the vicinity of the plane of junction between the partition wall and the solid electrolyte layer, the amount of alkali metals, alkaline earth metals, and silicon contained in the solid electrolyte layer is preferably reduced to a smallest possible extent. Specifically, when a portion of the solid electrolyte layer within 20 μm of the plane of junction between the partition wall and the solid electrolyte layer of the Ip cell is defined as a solid electrolyte layer junction portion, the total amount of alkali metals, alkaline earth metals, and silicon contained in the solid electrolyte layer junction portion is 2% by mass or less (more preferably 0 to 1.0% by mass, still more preferably 0 to 0.5% by mass) as reduced to their respective oxides, with respect to the solid electrolyte layer junction portion. Thus, the leakage of current between the electrodes of the Ip cell can be prevented more reliably, and the ion conductivity of the solid electrolyte layer can be improved.

Further, in order to reduce to a smallest possible extent the total amount of alkali metals, alkaline earth metals, and silicon contained in the solid electrolyte layer junction portion of the solid electrolyte layer which contains, as a predominant component, zirconia completely or partially stabilized by yttria, preferably, the following condition is satisfied. When a portion of the solid electrolyte layer excluding the solid electrolyte layer junction portion is defined as a solid electrolyte layer remaining portion, the total amount of alkali metals, alkaline earth metals, and silicon contained in the solid electrolyte layer remaining portion is 1% by mass or less as reduced to their respective oxides (more preferably 0 to 0.5% by mass, still more preferably 0 to 0.2% by mass) with respect to the entire solid electrolyte layer remaining portion.

The total amount of alkali metals, alkaline earth metals, and silicon contained in each of the partition wall junction portion and the solid electrolyte layer junction portion is obtained as follows. The element is embedded in resin, which is then cut along a plane perpendicular to the junction plane such that the partition wall, the solid electrolyte layer, and the junction plane are all exposed. Subsequently, after the cut surface is polished, three different regions are defined on each of the partition wall junction portion and the solid electrolyte layer junction portion appearing on the polished surface. In each of these regions, mass concentrations of 13 elements, including 6 alkali metals, 6 alkaline earth metals, and silicon, are measured by use of an X-ray probe microanalyzer (hereinafter referred to as "EPMA"). Subsequently, the mass concentrations of the individual elements measured for the three regions are averaged in order to obtain the average mass concentrations of the individual elements. Subsequently, the average mass concentrations of the individual elements are converted to values as reduced to their respective oxides, and the total sum of the converted average mass concentrations is calculated as the total amount of alkali metals, alkaline earth metals, and silicon. Notably, the above-described measurement is performed under vacuum by use of a wavelength dispersive X-ray spectrometer (WDS), with radiation current set to 0.25 nA and acceleration voltage set to 20 kV. An example of an EPMA is a model "JXA-8800M" available from JEOL DATUM LTD.

The total amount of alkali metals, alkaline earth metals, and silicon contained in each of the partition wall remaining portion (:meaning to exclude the junction portion of the partition) and the solid electrolyte layer remaining portion (meaning to exclude the junction portion of the solid electrolyte layer) is obtained as follows. As to the partition wall remaining portion, in the same manner as that used for measuring the junction portion, measurement is performed at three different points in a region extending up to 100 μm from the boundary between the partition wall junction portion and the partition wall remaining portion toward the inner side of the partition wall.

The element according to the present invention may assume a unitary structure in which all portions are integrated through firing (meaning simultaneous firing or cofiring), or a structure in which a plurality of portions having undergone firing are bonded together by use of heat-resisting cement or heat-resisting glass. An example of the structure in which a plurality of portions are bonded together is a structure in which an insulative base whose constituent portions have been integrated through firing and other portions having been integrated through firing are bonded together. However, in the case of the structure in which a plurality of portions are bonded together, in general, the individual portions must have sufficient mechanical strength before being bonded together and must be of sufficient thickness for supporting their own weights. Therefore, in many cases the overall size and thickness of the element increase. Therefore, when the element must have a small size, the element preferably assumes a unitary structure in which all portions are integrated through firing. This enables the individual portions to have a reduced thickness and size, and further, since heat-resisting cement, etc., which would otherwise being needed for bonding, is unnecessary and thermal conductivity is improved so that a period of time required for activating the individual cells to start gas measurement by the sensor element can be shortened further. Accordingly, use of the unitary element can be started immediately after startup of an internal combustion engine, and thus the degree of purification of exhaust gas can be improved. In particular, exhaust gas of automobiles, etc., which has been problematic in recent years, can be purified greatly when combustion efficiency is optimized immediately after startup. Therefore, shortening of the warm-up time is considerably important for purification of exhaust gas.

[2] Two-Cell-Type Sensor Element

An element according to the present invention which includes one Ip cell and one Vs cell will be described in detail with reference to FIGS. 1, 2, 4, and 5. Although an element (1a) of FIG. 1, an element (1b) of FIG. 4, and an element (1c) of FIG. 5 have different structures, respective portions which constitute these elements are denoted by the same reference numerals.

The element (1a) shown in FIG. 1 includes an insulative base (11) formed of an insulative ceramic member and containing a heating resistor (12) therein; and Ip and Vs cells joined directly to the insulative base (11). The Ip cell has a solid electrolyte layer (131) and a pair of electrodes (1322 and 1321) formed on a common surface of the solid electrolyte layer (131). The Vs cell has a solid electrolyte layer (141) and a pair of electrodes (1422 and 1421) formed on a common surface of the solid electrolyte layer (141). The element (1a) further includes a diffusion-chamber-forming member (161), a portion of which is formed by a rate-controlling introduction portion (163) made of a continuous-pore-type porous material, and another portion of which serves as a partition wall (162). The diffusion-chamber-forming member defines and forms a diffusion chamber (16).

The negative electrode (1321) of the Ip cell and the negative electrode (1421) of the Vs cell are formed on a common wall surface of the diffusion chamber. One end of the partition wall (162) is joined to the solid electrolyte layer (131) of the Ip cell and is located between the negative and positive electrodes (1321 and 1322) of the Ip cell. The positive electrode (1322) of the Ip cell is exposed to an atmosphere under measurement directly or indirectly (e.g., the case in which a protection layer is provided to prevent poisoning).

Figure 2:
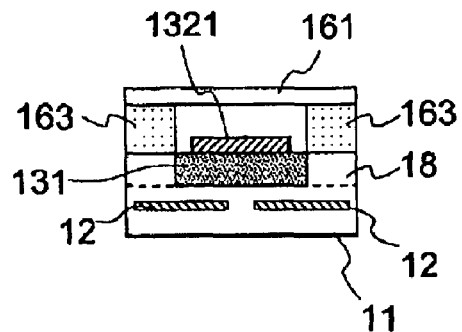
FIG. 2 is a schematic view of a cross section of the gas sensor elements shown in FIG. 1 or 6, taken along line A–A' therein.

The diffusion-chamber-forming member (161) covers the positive electrode (1422) of the Vs cell. In this structure, the positive electrode (1422) itself can charge oxygen of a predetermined pressure to pores of the positive electrode (1422) by applying a low constant current across the electrodes(1421/1422) of the Vs cell. The charged oxygen serves as a reference for oxygen concentration. FIG. 2 is a schematic sectional view of the element (1a) taken along line A–A' in FIG. 1. The rate-controlling introduction portion (163) indicated by dotted lines in FIG. 1 is disposed in a side wall of the element (1a) as shown in FIG. 2.

Figure 4:
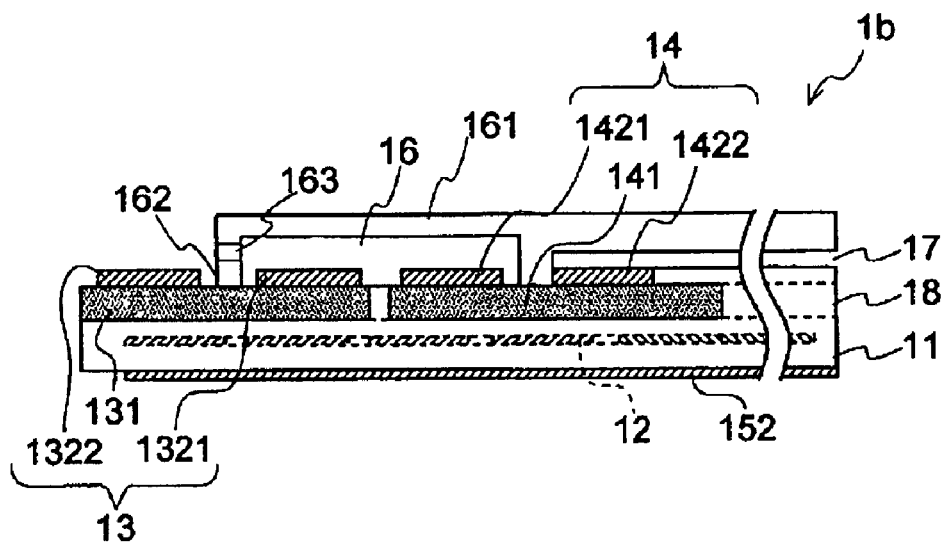
FIG. 4 is a schematic view showing a longitudinal cross section of another example of the gas sensor element of the present invention.
Figure 5:
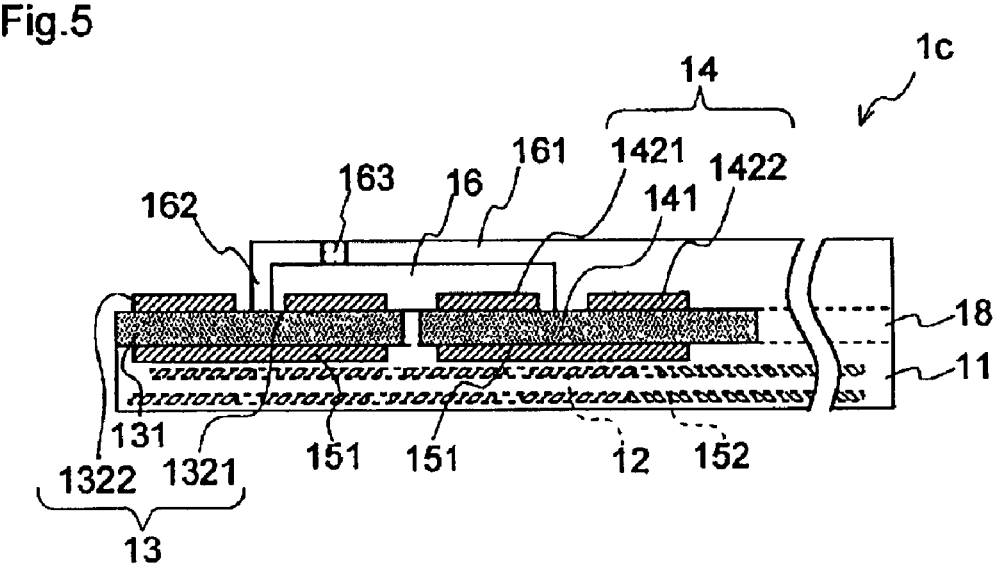
FIG. 5 is a schematic view showing a longitudinal cross section of still another example of the gas sensor element of the present invention.

The structure of the element (1a) may be modified as follows. The positions of the negative and positive electrodes (1321) and (1322) of the Ip cell may be reversed. As shown in FIG. 4, a reference gas introduction passage (17) may be provided for the positive electrode (1422) of the Vs cell, so that a reference gas can be used as a reference for oxygen concentration. As shown in FIG. 5, an auxiliary electrode (151) may be provided for the solid electrolyte layer (131) of the Ip cell and for the solid electrolyte layer (141) of the Vs cell.

As shown in FIG. 4, the rate-controlling introduction portion (163) may be provided in the partition wall (162). Alternatively, as shown in FIG. 5, the rate-controlling introduction portion (163) may be provided in a portion of the diffusion-chamber-forming member (161), the portion facing the Ip cell and the Vs cell. The rate-controlling introduction portion (163) may be a small through hole. As shown in FIG. 4, a migration prevention conductor (152) may be provided on one face of the insulative base (11). The migration prevention conductor (152) may assume a straight shape as shown in FIG. 4, or a meandering shape as shown in FIG. 5. As shown in FIG. 5, the migration prevention conductor (152) may be provided within the insulative base (11).

The element (1b) shown in FIG. 4 has the same configuration as that of the element (1a) shown in FIGS. 1 and 2, except for the following points. The rate-controlling introduction portion (163) is formed in the partition wall (162). A reference gas (e.g., atmospheric air) introduced from the reference gas introduction passage (17) to the positive electrode (1422) of the Vs cell serves as a reference for oxygen concentration. Further, a migration prevention conductor (152) is formed on one face of the insulative base (11).

The element (1c) shown in FIG. 5 has the same configuration as that of the element (1a) shown in FIGS. 1 and 2, except for the following points. The rate-controlling introduction portion (163) is provided in a portion of the diffusion-chamber-forming member (161), the portion facing the Ip cell and the Vs cell. An auxiliary electrode (151) is provided for the solid electrolyte layer (131) of the Ip cell and for the solid electrolyte layer (141) of the Vs cell. Moreover, a migration prevention conductor (152) of a meandering shape is provided within the insulative base (11).

[3] Three-Cell-Type Sensor Element

An element according to the present invention which includes two Ip cells and one Vs cell will be described in detail with reference to FIGS. 2 and 6 to 13. Although elements (1d, 1e, 1f, 1g, 1h, 1i, and 1j) shown in FIGS. 6 and 7 to 13, respectively, have different structures, respective portions which constitute these elements are denoted by the same reference numerals.

Figure 6:
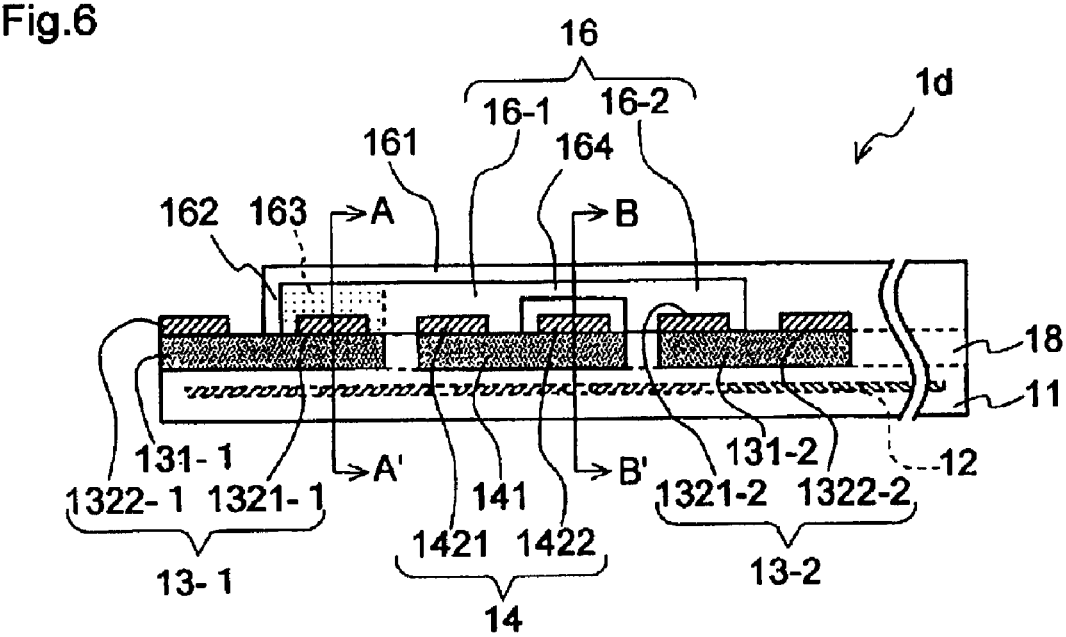
FIG. 6 is a schematic view showing a longitudinal cross section of still another example of the gas sensor element of the present invention.

The element (1d) shown in FIG. 6 includes an insulative base (11) formed of an insulative ceramic member and containing a heating resistor (12) therein; and a first Ip cell, a Vs cell, and a second Ip cell, which are joined directly to the insulative base (11). The first Ip cell has a solid electrolyte layer (131-1) and a pair of electrodes (1322-1 and 1321-1) formed on a common surface of the solid electrolyte layer (131-1). The Vs cell has a solid electrolyte layer (141) and a pair of electrodes (1422 and 1421) formed on a common surface of the solid electrolyte layer (141). The second Ip cell has a solid electrolyte layer (131-2) and a pair of electrodes (1322-2 and 1321-2) formed on a common surface of the solid electrolyte layer (131-2).

The element (1d) shown in FIG. 6 further includes a diffusion-chamber-forming member (161), a portion of which is formed by a rate-controlling introduction portion (163) made of a continuous-pore-type porous material, and another portion of which serves as a partition wall (162). The diffusion-chamber-forming member defines and forms a diffusion chamber (consisting of chamber sections 16-1 and 16-2). The negative electrode (1321-1) of the first Ip cell, the negative electrode (1421) of the Vs cell, and the negative electrode (1321-2) of the second Ip cell are formed on a common wall surface of the diffusion chamber. Although the positive electrode (1422) of the Vs cell is also formed on the common wall surface of the diffusion chamber, the electrode (1422) is sealed in an airtight manner by means of an electrode seal portion (153) such that the electrode (1422) is not exposed to the atmosphere within the diffusion chamber (consisting of chamber sections 16-1 and 16-2). Further, the partition wall (162) is joined to the solid electrolyte layer (131-1) of the first Ip cell and is located between the negative and positive electrodes (1321-1 and 1322-1) of the first Ip cell.

The positive electrode (1322-1) of the first Ip cell is exposed to an atmosphere under measurement directly or indirectly (e.g., the case in which a protection layer is provided to prevent poisoning). The positive electrode (1422) itself charges oxygen of a predetermined pressure into the boundary between the solid electrolyte (141) and the positive electrode (1422), so that the charged oxygen serves as a reference for oxygen concentration. The electrode seal portion (153), which seals the positive electrode (1422) of the Vs cell, projects into the diffusion chamber (consisting of chamber sections 16-1 and 16-2) to thereby form a narrowed portion, which serves as a nitrogen-oxide rate-controlling portion (164). A portion of the diffusion chamber located on the first Ip cell side with respect to the nitrogen-oxide rate-controlling portion (164) serves as a first diffusion chamber section (161), and a portion of the diffusion chamber located on the second Ip cell side with respect to the nitrogen-oxide rate-controlling portion (164) serves as a second diffusion chamber section (16-2).

Figure 7:
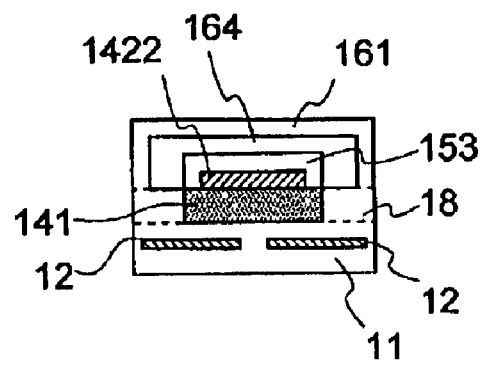
FIG. 7 is a schematic view of a cross section of the gas sensor element shown in FIG. 6, taken along line B–B' therein.

FIG. 2 is a schematic sectional view of the element (1d) taken along line A–A' in FIG. 6. The rate-controlling introduction portion (163) indicated by dotted lines in FIG. 6 is disposed in a side wall of the element (1d) as shown in FIG. 2. FIG. 7 is a schematic sectional view of the element (1d) taken along line B–B' in FIG. 6.

Figure 10:
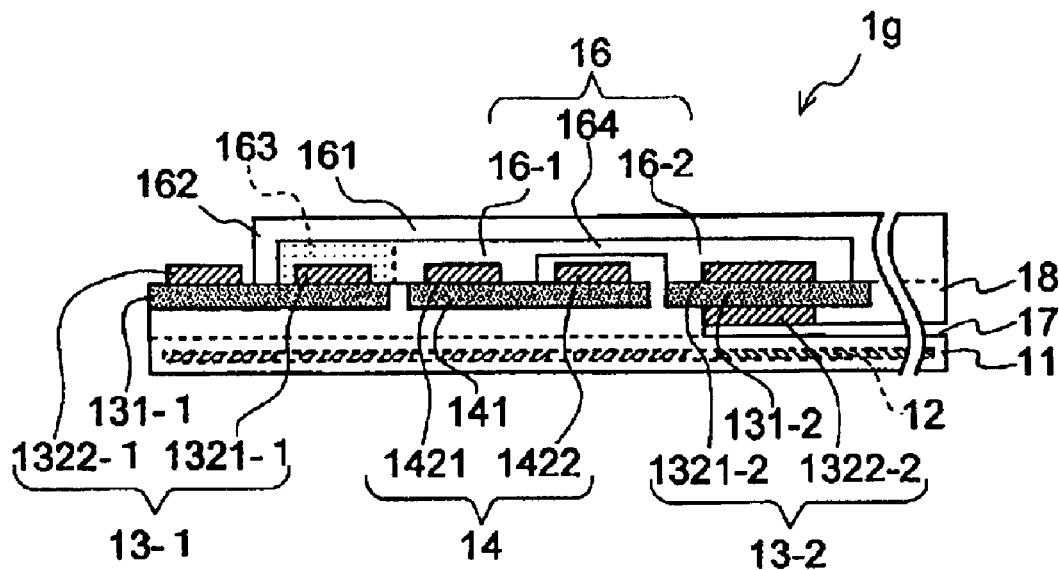
FIG. 10 is a schematic view showing a longitudinal cross section of still another example of the gas sensor element of the present invention.

The structure of the element (1d) may be modified as follows. The positions of the negative and positive electrodes (1321-1) and (1322-1) of the first Ip cell may be reversed; and the positions of the negative and positive electrodes (1321-2) and (1322-2) of second Ip cell may be reversed. A reference gas introduction passage may be provided for the positive electrode (1422) of the Vs cell, so that a reference gas can be used as a reference for oxygen concentration. Further, as shown in FIG. 10, a reference gas introduction passage may be provided for one of the electrodes (1321-2 or 1322-2) of the second Ip cell, so that a reference gas can be used as a reference for oxygen concentration.

Figure 8:
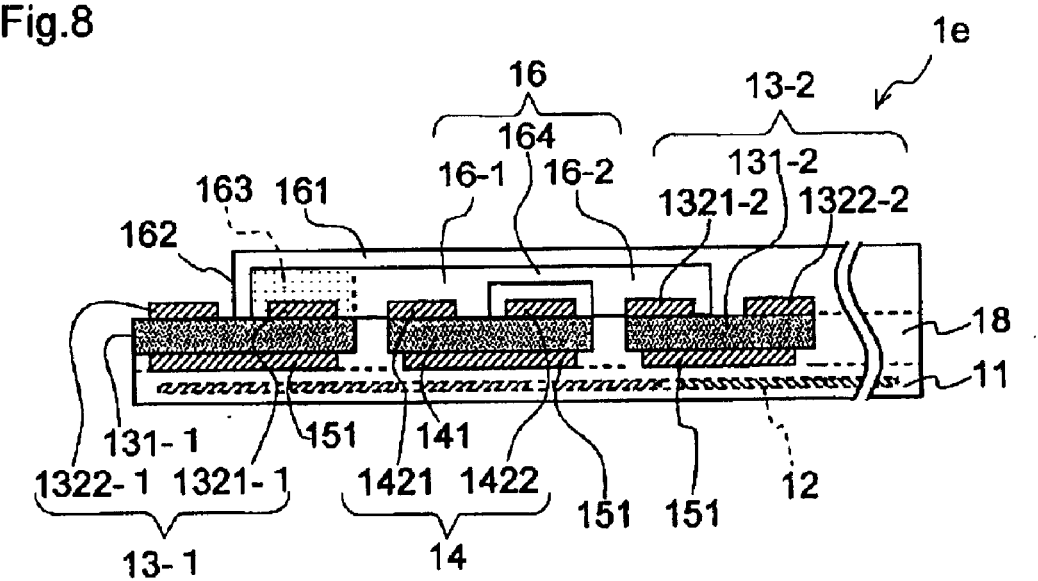
FIG. 8 is a schematic view showing a longitudinal cross section of still another example of the gas sensor element of the present invention.

As shown in FIG. 8, an auxiliary electrode (151) may be provided for the solid electrolyte layer (131-1) of the first Ip cell, for the solid electrolyte layer (141) of the Vs cell, and for the solid electrolyte layer (131-2) of the second Ip cell. As shown in FIG. 4, the rate-controlling introduction portion (163) may be provided in the partition wall (162). Alternatively, as shown in FIG. 5, the rate-controlling introduction portion (163) may be provided in a portion of the diffusion-chamber-forming member (161), the portion facing the Ip cell and the Vs cell. The rate-controlling introduction portion (163) may be a small through hole. As shown in FIG. 4, a migration prevention conductor (152) may be provided on one face of the insulative base (11).

Figure 11:
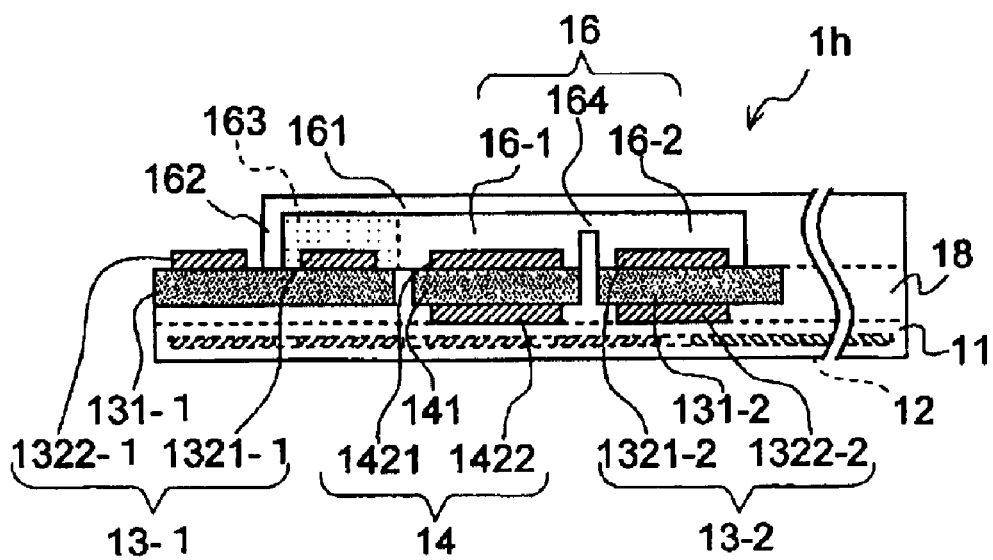
FIG. 11 is a schematic view showing a longitudinal cross section of still another example of the gas sensor element of the present invention.
Figure 12:
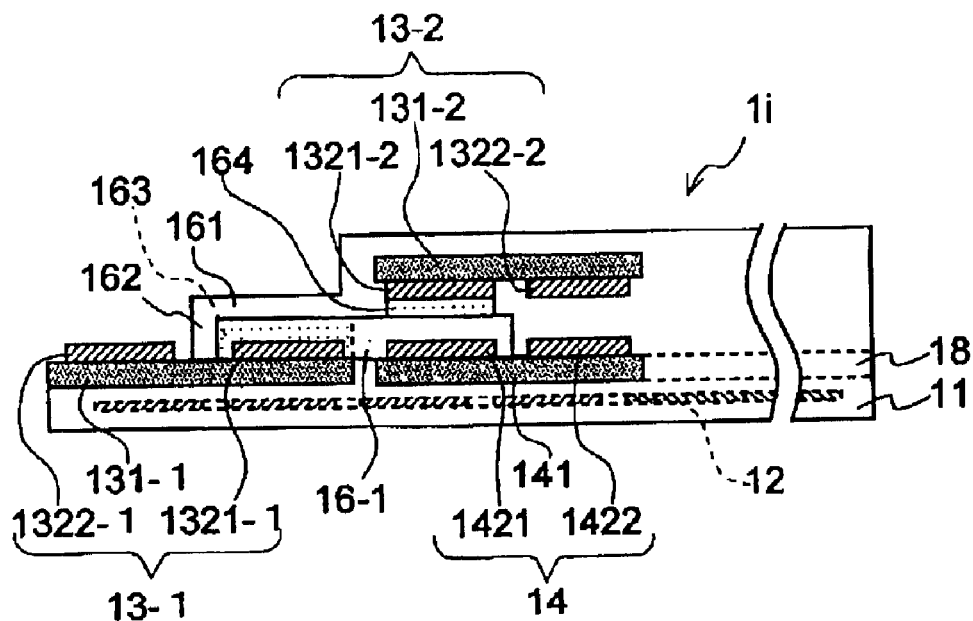
FIG. 12 is a schematic view showing a longitudinal cross section of still another example of the gas sensor element of the present invention.
Figure 13:
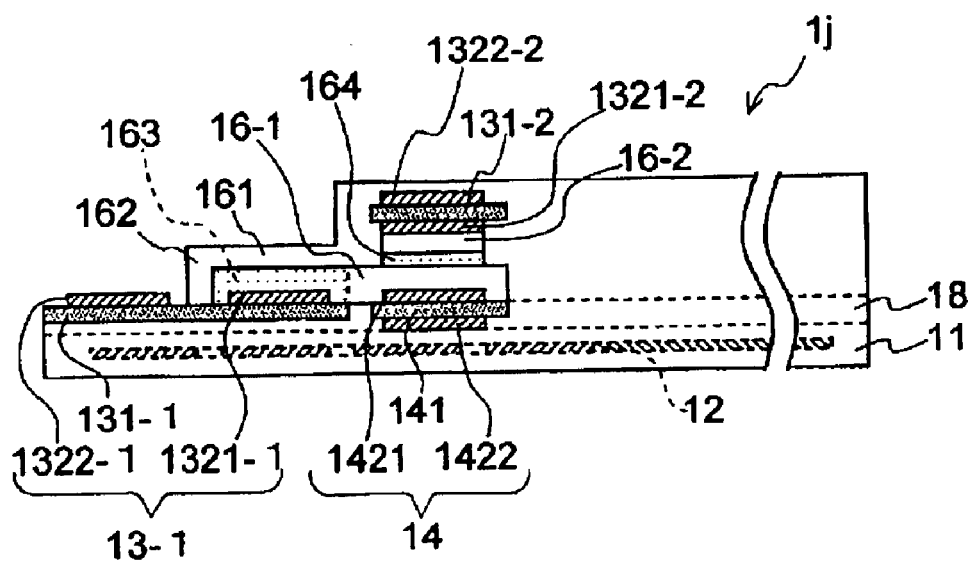
FIG. 13 is a schematic view showing a longitudinal cross section of still another example of the gas sensor element of the present invention.
Figure 14:
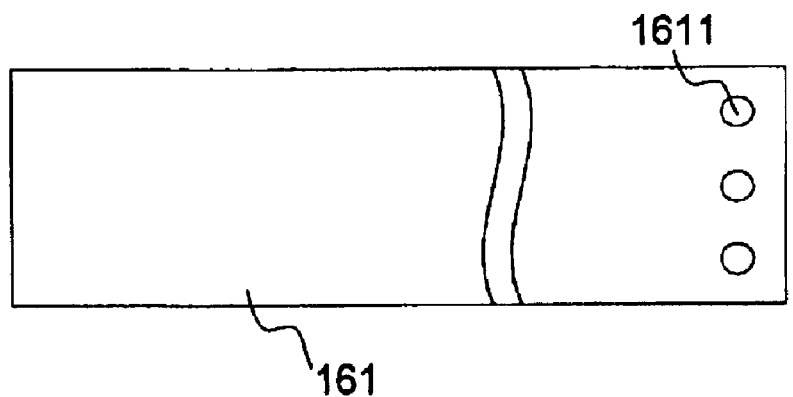
FIG. 14 is an explanatory view showing the planar shape of the green diffusion-chamber-forming member used in the Examples.
Figure 15:
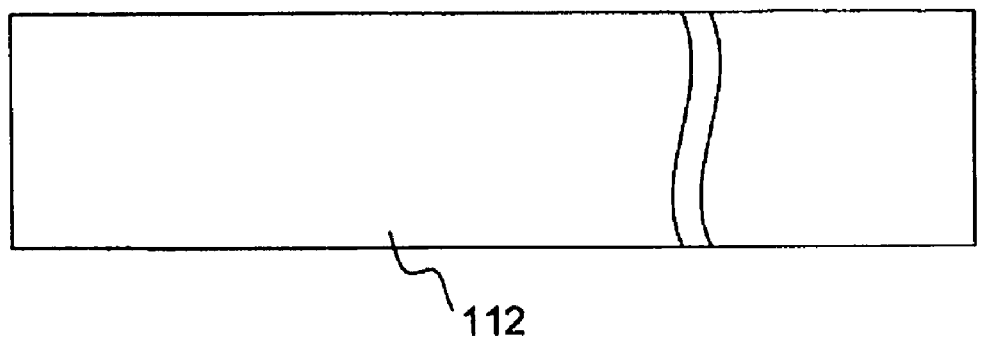
FIG. 15 is an explanatory view showing the planar shape of the green insulative base upper layer used in the Examples.

The migration prevention conductor (152) may assume a straight shape as shown in FIG. 4 or a meandering shape as shown in FIG. 5. As shown in FIG. 5, the migration prevention conductor (152) may be provided within the insulative base (11). Instead of using the electrode seal portion (153), the nitrogen-oxide rate-controlling portion (164) may be formed by narrowing a portion of the diffusion chamber by use of another member as shown in FIG. 11. Alternatively, as shown in FIG. 13, the nitrogen-oxide rate-controlling portion (164) may be formed by use of a continuous-pore-type porous material. Further, as shown in FIG. 12, only the nitrogen-oxide rate-controlling portion (164) formed of a continuous-pore-type porous material is provided, without provision of the second diffusion chamber section. As shown in FIGS. 12 and 13, the second Ip cell may be provided on an inner wall surface of the diffusion chamber different from the inner wall surface on which the first Ip cell and the Vs cell are provided.

The element (1e) shown in FIG. 8 has the same configuration as that of the element (1d) shown in FIGS. 6 and 7, except for the following points. An auxiliary electrode (151) is provided for the solid electrolyte layer (131-1) of the first Ip cell, for the solid electrolyte layer (141) of the Vs cell, and for the solid electrolyte layer (131-2) of the second Ip cell.

Figure 9:
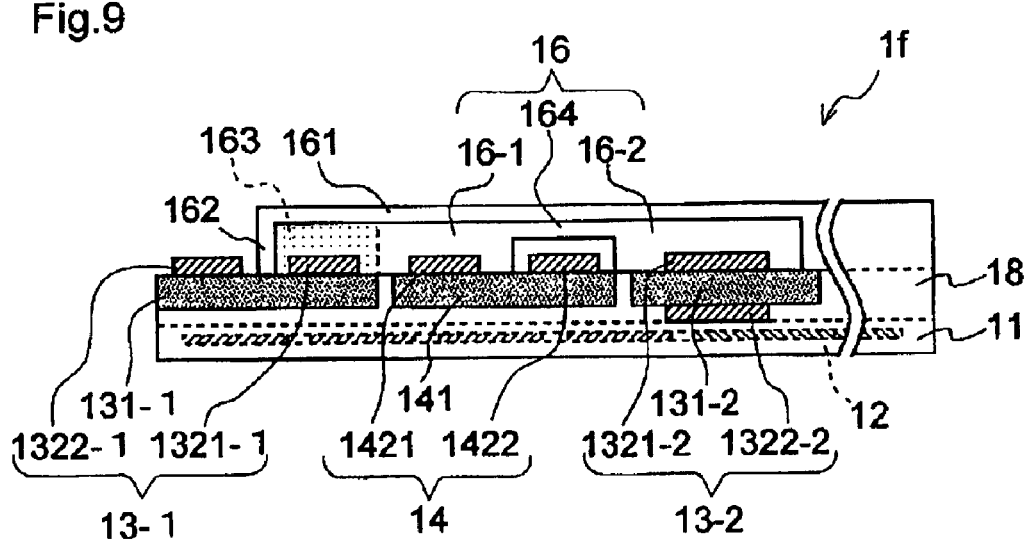
FIG. 9 is a schematic view showing a longitudinal cross section of still another example of the gas sensor element of the present invention.

The element (1f) shown in FIG. 9 has the same configuration as that of the element (1d) shown in FIGS. 6 and 7, except for the following points. The positive electrode (1322-2) of the second Ip cell is formed between the insulative base (11) and the solid electrolyte layer (131-2) of the second Ip cell.

The element (1g) shown in FIG. 10 has the same configuration as that of the element (1d) shown in FIGS. 6 and 7, except for the following points. A reference gas introduction passage (17) is provided for the positive electrode of the second Ip cell, so that a reference gas can be used as a reference for oxygen concentration.

The element (1h) shown in FIG. 11 has the same configuration as that of the element (1d) shown in FIGS. 6 and 7, except for the following points. The positive electrode (1422) of the Vs cell is formed between the insulative base (11) and the solid electrolyte layer (141) of the Vs cell. Similarly, the positive electrode of the second Ip cell is formed between the insulative base (11) and the solid electrolyte layer (131-2) of the second Ip cell. Further, instead of using the electrode seal portion (153), the nitrogen-oxide rate-controlling portion (164) is formed by use of another member.

The element (1i) shown in FIG. 12 has the same configuration as that of the element (1d) shown in FIGS. 6 and 7, except for the following points. The second Ip cell is provided on an inner wall surface of the diffusion chamber different from the inner wall surface on which the first Ip cell and the Vs cell are provided, such that the second Ip cell is disposed above the Vs cell. The element (1i) does not have the second diffusion chamber section and has only a nitrogen-oxide rate-controlling portion (164) formed of a continuous-pore-type porous material. Even when only the nitrogen-oxide rate-controlling portion (164) is provided, measurement at the second Ip cell is possible.

The element (1j) shown in FIG. 13 has the same configuration as that of the element (1d) shown in FIGS. 6 and 7, except for the following points. The second Ip cell is provided on an inner wall surface of the diffusion chamber different from the inner wall surface on which the first Ip cell and the Vs cell are provided, such that the second Ip cell is disposed above the Vs cell. The second diffusion chamber section (16-2) is partitioned by means of a nitrogen-oxide rate-controlling portion (164) formed of a continuous-pore-type porous material. The positive electrode (1422) of the Vs cell is formed between the insulative base (11) and the solid electrolyte layer (141) of the Vs cell.

As described above, a three-cell-type element can include a first Ip cell and a second Ip cell. Of these cells, the first Ip cell pumps outside of the diffusion chamber oxygen contained in a gas under measurement introduced into the diffusion chamber (including oxygen dissociated from a portion of nitrogen oxides) to thereby reduce the oxygen concentration of the gas under measurement introduced into the diffusion chamber. The second Ip cell applies to the gas under measurement, introduced into the diffusion chamber having a reduced oxygen concentration, a voltage having a level which decomposes nitrogen oxides only. As a result, only oxygen generated through decomposition of nitrogen oxides is pumped outside the diffusion chamber via the solid electrolyte layer of the second Ip cell, to output a current that flows at that time.

The first and second Ip cells may have a positional relation within the element such that the first Ip cell is located upstream of the second Ip cell with respect to the flow direction of the gas under measurement introduced into the diffusion chamber.

In the three-cell type element, the oxygen concentration within the diffusion chamber having been reduced by means of the first Ip cell is measured using the Vs cell; and an amount of oxygen that the first Ip cell has failed to remove is subtracted from an amount of oxygen pumped out by means of the second Ip cell for the purpose of correction, whereby precise concentration of nitrogen oxides is measured. The Vs cell of the three-cell type element contributes to such a correction operation. Moreover, the concentration of oxygen diffused in the vicinity of the second Ip cell is monitored using the Vs cell for the purpose of feedback control for maintaining constant the concentration of oxygen contained in the gas under measurement whose oxygen concentration has been reduced by means of the first Ip cell. The Vs cell of the three-cell type element contributes to such a feedback operation as well.

Therefore, the Vs cell is disposed between the first and second Ip cells, which are disposed such that the first Ip cell is located upstream of the second Ip cell with respect to the direction of diffusion of the gas under measurement.

Each of other gas sensor elements according to an aspect of the present invention includes the above-described insulative base (11), heating resistor (12), oxygen pump cell (13), oxygen detection cell (14), rate-controlling introduction portion (163), diffusion chamber (16), diffusion-chamber-forming member (161), and partition wall (162), and satisfies the following conditions (a), (b), (c) and (d):

(a) each of the insulative base (11) and the diffusion-chamber-forming member (161) contains alumina as a predominant component;

(b) a partition wall (162), which extends from the diffusion-chamber-forming member (161), is joined to a surface of a solid electrolyte (131) between a pair of electrodes (1321/1322) of the oxygen detection cell; and (c) a boundary portion within 20 μm from a plane of the junction between the solid electrolyte layer (131) and the partition wall (162) contains no portion in which the amount of substances other than alumina exceeds by 2% by mass or more the amount of substances, other than alumina, of the diffusion-chamber-forming member (161); and (d) the insulative base (11), the heating resistor (12), the solid electrolyte layers (131, 132), the electrodes (1321, 1322, 1421, 1422) and the diffusion-chamber-forming member (161) are unitarily integrated through simultaneous firing.

Notably, as to the condition (b), the partition wall (162), which extends from the diffusion-chamber-forming member (161), may be a part of a cover which covers the diffusion chamber. The condition (c) means that the amount of the latter predetermined components is not greater than 2% by mass of the amount of the former predetermined components. The amount of components other than the alumina can be measured by use of, for example, EPMA, as described above. The condition (c) is important because a large amount of oxygen ions must flow in a planer direction through the planer electrolyte under a high voltage applied forcibly across the electrodes of the pumping cell (Ip cell) in this type of sensor structure.

Each of the solid electrolyte layers (131 and 132) may contain zirconia ceramic in an amount of 20 to 90% by mass and alumina in an amount of 10 to 80% by mass. The zirconia ceramic mentioned here is identical to the zirconia contained in the above-described solid electrolyte layer. The migration prevention conductor (152) is the same as described above.

[4] Gas Sensor

A gas sensor according to the present invention includes a gas sensor element according to the present invention. No particular limitation is imposed on the remaining portion of the gas sensor. For example, the gas sensor may include armor (e.g., a protector, outer sleeve, and grommet) for protecting the gas sensor element from water, shock, etc., applied from the outside. Further, the gas sensor may include a metallic shell having a threaded portion for attaching the gas sensor to, for example, an exhaust pipe. Moreover, a holder for fixedly holding the gas sensor element and a buffer material (for buffering heat and shock) may be provided within the metallic shell. Further, the gas sensor may include lead members (e.g., lead frames and lead wires) for extracting an electrical signal from the gas sensor element and for applying voltage to the heating resistor.

EXAMPLES

The present invention will be described in further detail with reference to FIGS. 14 to 30.

Note that, in order to facilitate understanding, in the following description some portions are denoted by the same reference numerals before and after firing. Although a production process is described as if a single element were fabricated, in an actual process, green sheets which can produce ten green elements each having a length of 60 mm and a width of 5 mm (after firing, having a length of about 47 mm and a width of about 3.9 mm) by cutting are prepared; a pattern for 10 elements is printed on each of the green sheets; and the green sheets are stacked to form a laminate, from which green sensor elements are cut out. Moreover, positioning holes are formed in each green sheet along the peripheral edge thereof, and fixing pins are passed through these holes to thereby position each green sheet.

Figure 16:
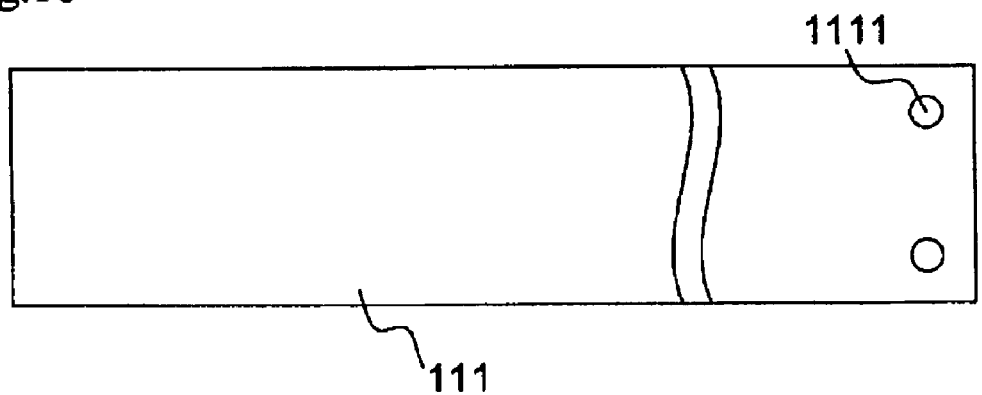
FIG. 16 is an explanatory view showing the planar shape of the green insulative base lower layer used in the Examples.
Figure 17:
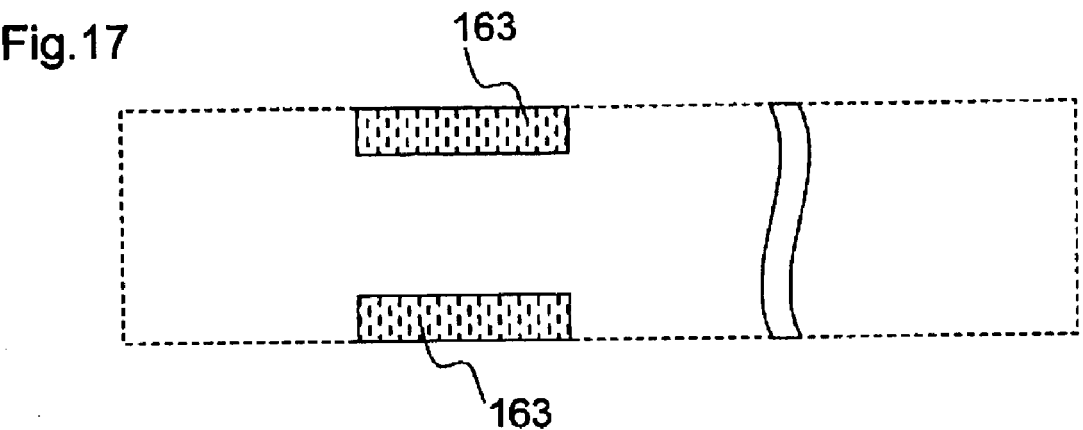
FIG. 17 is an explanatory view showing the planar shape of the green rate-controlling introduction portion used in the Examples.
Figure 18:
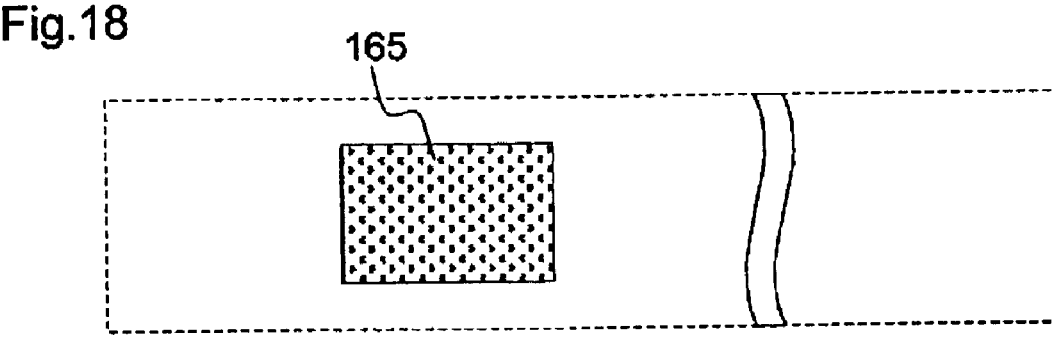
FIG. 18 is an explanatory view showing the planar shape of the to-be-burned member for the diffusion chamber used in the Examples.

In FIGS. 17 to 30, the peripheral edge of a green insulative base lower layer (111) shown in FIG. 16 is shown by a dotted line in order to show the stacked position of each green body as viewed from above. Further, in FIG. 31, the positions of electrode surfaces (portions excluding lead portions) of individual electrodes are shown by dotted lines in order to show the positions of the electrode surfaces as viewed from a side of the green sensor element.

[1] Fabrication of a Full-Range Air-Fuel-Ratio Sensor Element

<1> Preparation of Five Types of Green Ceramic Sheets (1) Preparation of a Green Diffusion-Chamber-Forming Member (161)

Alumina powder (purity: not less than 99.99%), butyral resin serving as a binder, dibutyl phthalate serving as a plasticizer, and toluene and methyl ethyl keton serving as solvents were mixed to yield a slurry. Subsequently, a sheet having a thickness of 0.2 mm was formed from the slurry by a doctor blade process. Subsequently, three though-holes (1611) were formed at predetermined positions at one end portion of the sheet. Thus, a green diffusion-chamber-forming member (161) of a planar shape shown in FIG. 14 was obtained.

(2) Preparation of a Green Insulative Base Upper Layer (112)

A slurry was prepared in the same manner as described in (1) above, and a sheet having a thickness of 0.4 mm was formed from the slurry by a doctor blade process. Thus, a green insulative base upper layer (112) of a planar shape shown in FIG. 15 was obtained.

(3) Preparation of a Green Insulative Base Lower Layer (111)

A slurry was prepared in the same manner as described in (1) above, and a sheet having a thickness of 0.8 mm was formed from the slurry by a doctor blade process. Subsequently, two though-holes (1111) were formed in the sheet. Thus, a green insulative base lower layer (111) of a planar shape shown in FIG. 16 was obtained.

(4) Preparation of a Green Partition Wall (162)

A slurry was prepared in the same manner as described in (1) above, and a sheet having a thickness of 150 μm was formed from the slurry by a doctor blade process. Thus, a green partition wall (162) of a planar shape shown in FIG. 29 was obtained. This green partition wall (162) was integrated with the green diffusion-chamber-forming member (161) in the course of firing to become a portion of the diffusion-chamber-forming member (161) after firing.

(5) Preparation of a Green Fourth Insulating Layer (166)

A slurry was prepared in the same manner as described in (1) above, and a sheet having a thickness of 150 μm was formed from the slurry by a doctor blade process. Subsequently, two though-holes (1661) were formed in the sheet. Thus, a green fourth insulating layer (166) of a planar shape shown in FIG. 30 was obtained. This green fourth insulating layer (166) was integrated with the green diffusion-chamber-forming member (161) in the course of firing to become a portion of the diffusion-chamber-forming member (161) after firing.

<2> Green Laminate Forming Process (1) Formation of a Green Ip Cell Solid Electrolyte Layer Lower (1311) and a Green Vs Cell Solid Electrolyte Layer Lower (1411)

A mixture of 70% by mass zirconia powder (purity: not less than 99.99%) and 30% by mass alumina powder (purity: not less than 99.99%, average particle size: 0.6 μm) and a dispersant were mixed together in acetone to yield a slurry. Separately, butyral resin (binder), butyl carbitol, dibutyl phthalate (plasticizer), and acetone were mixed to obtain a binder solution. This binder solution was added to the slurry, which was kneaded to allow acetone to vaporize, to thereby prepare a solid electrolyte layer paste.

Figure 20:
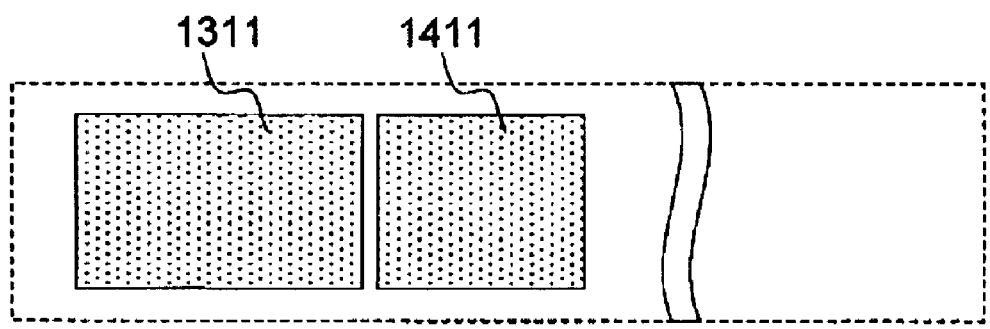
FIG. 20 is an explanatory view showing the planar shapes of the green Ip cell solid electrolyte layer lower and the green Vs cell solid electrolyte layer lower used in the Examples.

The thus-prepared solid electrolyte layer paste was applied through screen printing onto the surface of the green insulative base upper layer (112) obtained in <1> (2) above such that layers of the paste (thickness of 40 μm) having planar shapes shown in FIG. 20 were formed on the surface. Subsequently, the layers were dried to thereby yield a green Ip cell solid electrolyte lower layer (1311) and a green Vs cell solid electrolyte lower layer (1411).

(2) Formation of a Green First Insulating Layer (181)

Alumina powder (purity: not less than 99.99%), butyral resin serving as a binder, dibutyl phthalate serving as a plasticizer, and toluene and methyl ethyl keton serving as solvents were mixed to yield a paste. Further, predetermined amounts of butyl carbitol and acetone were added to the paste, which was then mixed for four hours in order to evaporate acetone, to thereby prepare an insulating layer paste.

Figure 21:
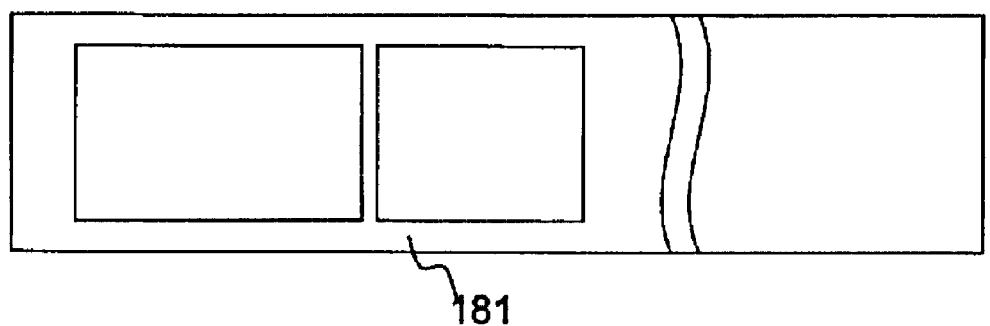
FIG. 21 is an explanatory view showing the planar shape of the green first insulating layer used in the Examples.

The thus-prepared insulating layer paste was applied through screen printing onto the green insulative base upper layer (112) such that a layer of the paste (thickness of 40 μm) having a planar shape shown in FIG. 21 was formed over the entire surface, excepting the green Ip cell solid electrolyte layer lower (1311) and the green Vs cell solid electrolyte layer lower (1411) formed in (1) above. Thus, the green first insulating layer (181) was formed.

(3) Formation of a Green Ip Cell Solid Electrolyte Layer Upper (1312) and a Green Vs Cell Solid Electrolyte Layer Upper (1412)

Figure 22:
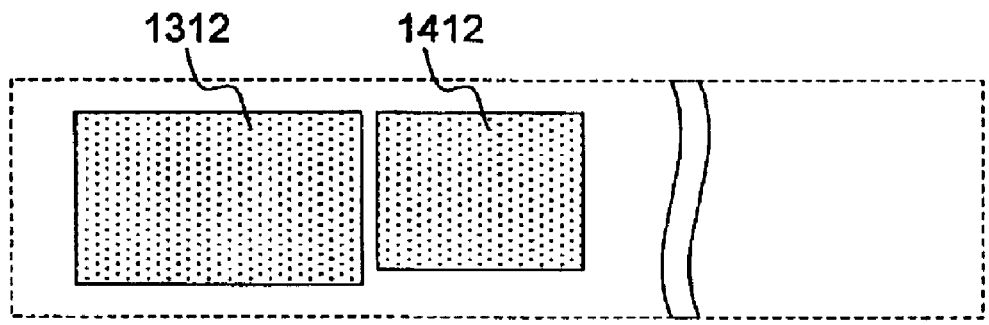
FIG. 22 is an explanatory view showing the planar shapes of the green Ip cell solid electrolyte upper layer and the green Vs cell solid electrolyte upper layer used in the Examples.

The solid electrolyte layer paste used in (1) above was applied through screen printing onto the green Ip cell solid electrolyte lower layer (1311) and the green Vs cell solid electrolyte lower layer (1411) such that layers of the paste (thickness of 30 μm) having planar shapes shown in FIG. 22 were formed thereon. Subsequently, the layers were dried to thereby form the green Ip cell solid electrolyte upper layer (1312) and the green Vs cell solid electrolyte upper layer (1412).

(4) Formation of a Green Second Insulating Layer (182)

Figure 23:
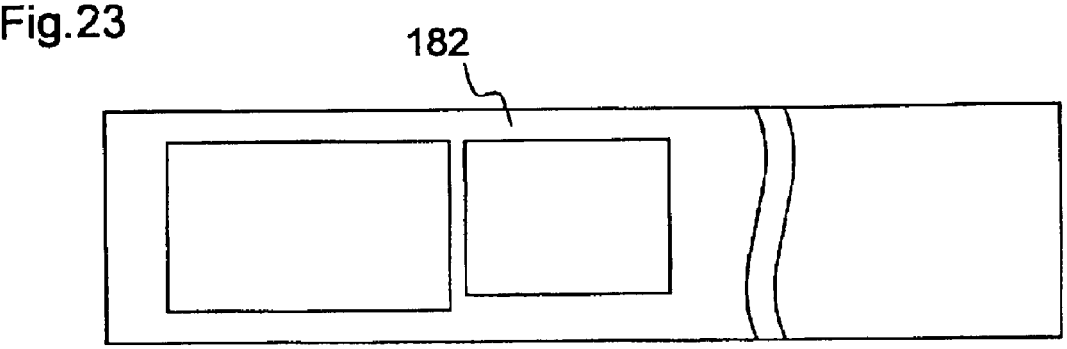
FIG. 23 is an explanatory view showing the planar shape of the green second insulating layer used in the Examples.

The insulating layer paste used in (2) above was applied through screen printing onto the green first insulating layer (181) such that a layer of the paste (thickness of 30 μm) having a planar shape shown in FIG. 23 was formed over the entire surface, excepting the green Ip cell solid electrolyte layer upper (1312) and the green Vs cell solid electrolyte layer upper (1412). Subsequently, the layer was dried to thereby form the green second insulating layer (182).

(5) Formation of a Green Common Negative Electrode (134) for the Ip and Vs Cells and a Green Positive Electrode (1422) for the Vs Cell 15 parts by mass zirconia powder obtained through coprecipitation (containing 5.4 mol % $Y_2O_3$ serving as a stabilizer and having an average particle size of 0.3 to 0.4 μm) and 100 parts by mass platinum powder were mixed to thereby prepare a conductive layer paste.

Figure 19:
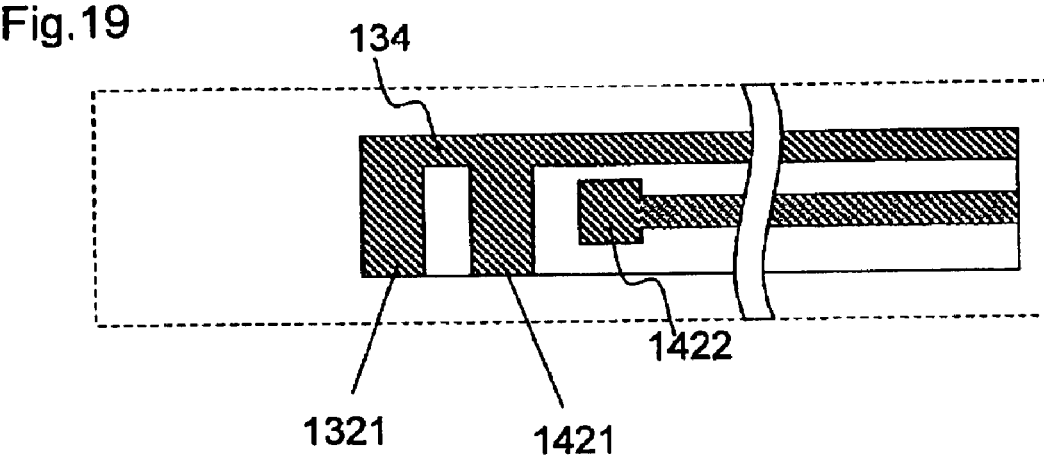
FIG. 19 is an explanatory view showing the planar shapes of the green common negative electrode for the Ip and Vs cells and the green positive electrode for the Vs cell used in the Examples.

The thus-prepared conductive layer paste was applied through screen printing onto the green Ip cell solid electrolyte upper layer (1312), the green Vs cell solid electrolyte upper layer (1412), and the green second insulating layer (182) such that layers of the paste (thickness of 20 μm) having planar shapes shown in FIG. 19 were formed thereon. Subsequently, the layers were dried to thereby form the green common negative electrode (134) for the Ip and Vs cells and the green positive electrode (1422) for the Vs cell. The green common negative electrode (134) has branched end portions (electrode portions), one of which is in contact with the green Ip cell solid electrolyte upper layer (1312) and the other of which is in contact with the green Vs cell solid electrolyte upper layer (1412). Further, the green positive electrode (1422) for the Vs cell is in contact with the green Vs cell solid electrolyte layer upper (1412).

(6) Formation of a Green Third Insulating Layer (183)

Figure 28:
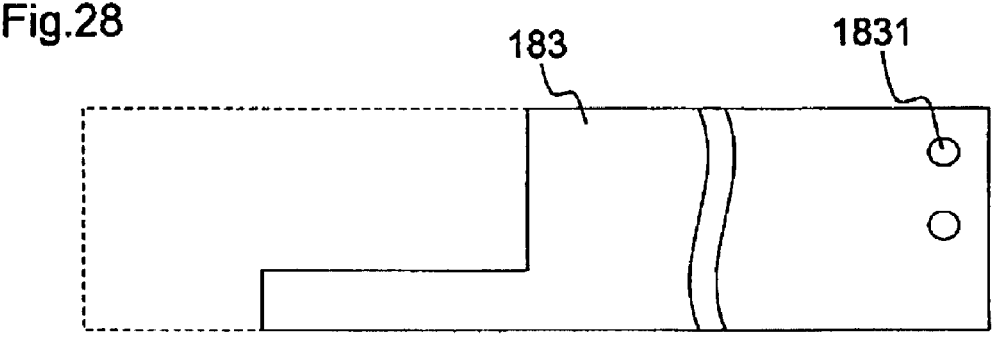
FIG. 28 is an explanatory view showing the planar shape of the green third insulating layer used in the Examples.
Figure 29:
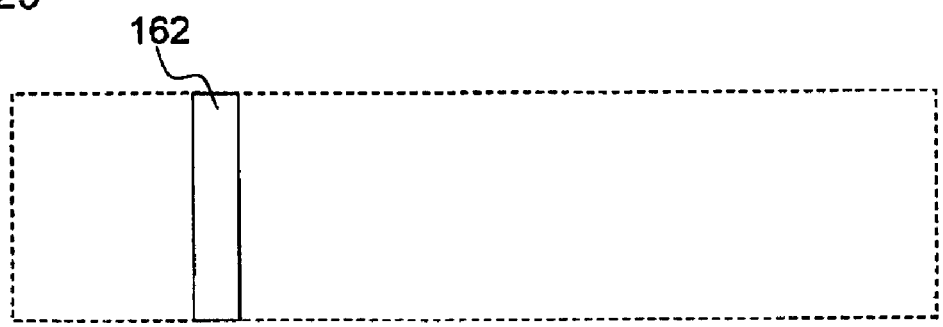
FIG. 29 is an explanatory view showing the planar shape of the green partition wall used in the Examples.
Figure 30:
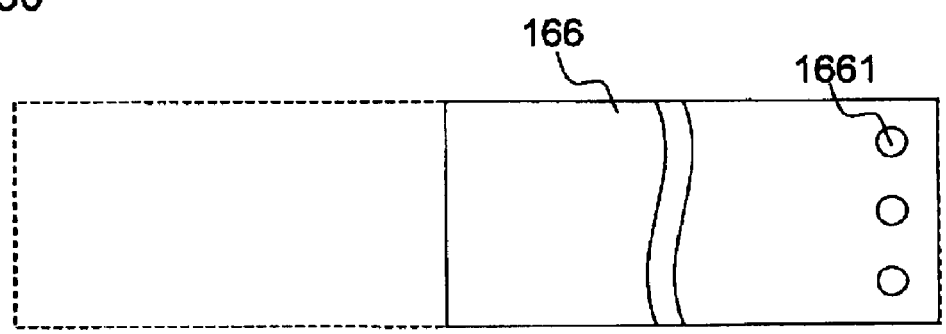
FIG. 30 is an explanatory view showing the planar shape of the green fourth insulating layer used in the Examples.

The insulating layer paste used in (2) above was applied through screen printing such that a layer of the paste (thickness of 30 μm) having a planar shape (a through hole 1831 is provided) shown in FIG. 28 was formed to prevent the green common negative electrode (134) for the Ip and Vs cells and the green positive electrode (1422) for the Vs cell, formed in (5) above, from coming into direct contact with a green positive electrode (1322) for the Ip cell to be formed later. The paste layer was dried to form the green third insulating layer (183).

(7) Formation of a Green Positive Electrode (1322) for the Ip Cell

Figure 24:
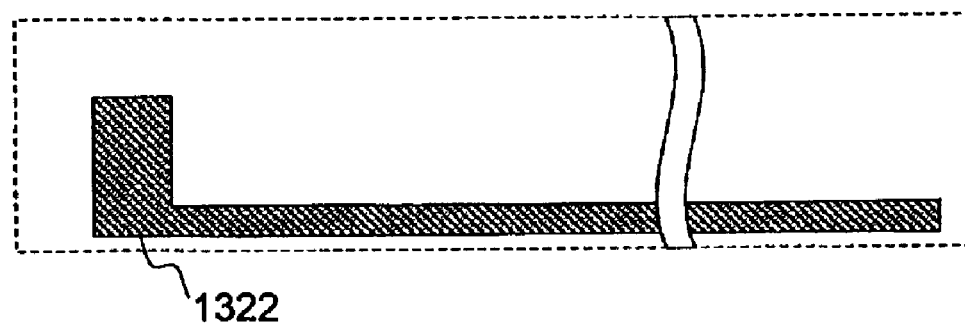
FIG. 24 is an explanatory view showing the planar shape of the green positive electrode for the Ip cell used in the Examples.

The conductive layer paste used in (5) above was applied through screen printing such that a layer of the paste (thickness of 20 μm) having a planar shape shown in FIG. 24 was formed in contact with the green Ip cell solid electrolyte upper layer (1312) without coming into contact with the green Vs cell solid electrolyte upper layer (1412). Subsequently, the layer was dried to thereby form the green positive electrode (1322) for the Ip cell.

(8) Formation of a to-be-Burned Member (165) for the Diffusion Chamber

Carbon powder, butyral resin serving as a binder, dibutyl phthalate serving as a plasticizer, and toluene and methyl ethyl keton serving as solvents were mixed to prepare a to-be-burned member paste. This to-be-burned member paste was applied through screen printing onto an electrode portion (i.e., a portion other than a lead portion) of the green common negative electrode (134) for the Ip, Vs cells and an electrode portion of the green positive electrode (1422) for the Vs cell, the green Ip cell solid electrolyte layer upper (1312), and the green Vs cell solid electrolyte layer upper (1412) in such a manner that a layer of the paste (thickness of 150 μm) having a planar shape shown in FIG. 18 was formed thereon. The paste layer was dried to form the to-be-burned member (165) for the diffusion chamber.

(9) Formation of a Green Rate-Controlling Introduction Portion (163)

Alumina powder (purity: not less than 99.99%), butyral resin serving as a binder, dibutyl phthalate serving as a plasticizer, and toluene and methyl ethyl keton serving as solvents were mixed to prepare a paste. Further, predetermined amounts of butyl carbitol and acetone were added to the paste, which was then mixed for four hours to evaporate acetone, to thereby prepare a paste, to which carbon powder having an average particle size of 5 μm was mixed in an amount of 45% by volume with respect to the volume of alumina. Thus, a porous portion paste was prepared. This porous portion paste was applied through screen printing at the same position as that of the to-be-burned member (165) along the longitudinal direction of the element but at a position not overlapping the to-be-burned member (165) along the width direction of the element, such that layers of the porous portion paste (thickness of 100 μm) having a planar shape shown in FIG. 17 was formed. The paste layer was dried to form the green rate-controlling introduction portion (163). Although the green rate-controlling introduction portion (163) differs in thickness from the to-be-burned member (165), they assume the same thickness in the course of stacking and compression of the green diffusion-chamber-forming member (161).

(10) Stacking of the Green Partition Wall (162)

Figure 31:
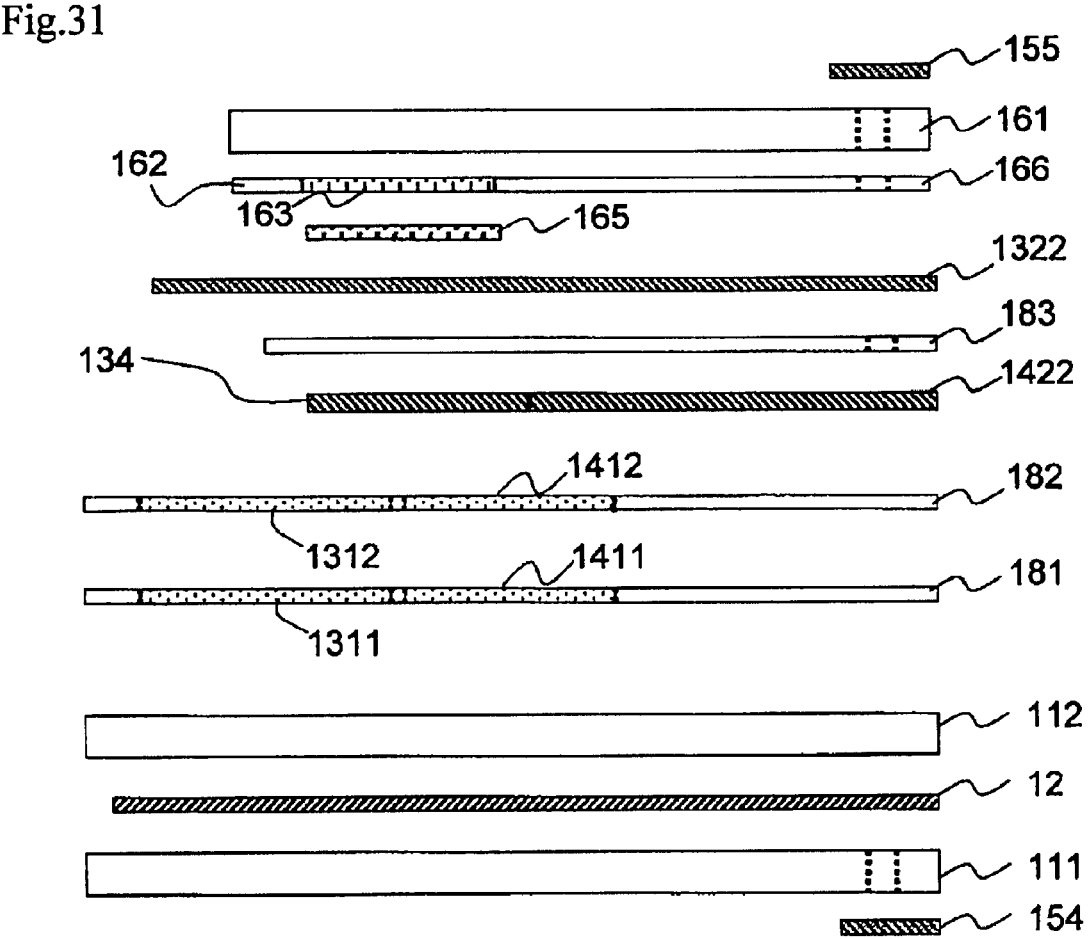
FIG. 31 is an explanatory view showing the green gas sensor element from its side in order to show the relation among the stacked layers shown in FIGS. 14 to 30.

By use of a mixture solution of secondary butanol and butyl carbitol, the green partition wall (162) prepared in <1> (4) above was stacked on and pressure-bonded to the laminate obtained through processes up to the above-described step (9) on the side on which the green positive electrode (1322) for the Ip cell was formed, such that the green partition wall (162) was located between the positive electrode (1322) of the Ip cell and the negative electrode of the Ip cell after firing (see FIG. 31).

(11) Stacking of the Green Fourth Insulating Layer (166)

By use of a mixture solution of secondary butanol and butyl carbitol, the green fourth insulating layer (166) prepared in <1> (5) above was stacked on and pressure-bonded to the laminate obtained through processes up to the above-described step (10) on the side on which the green positive electrode (1322) for the Ip cell was formed, such that the green fourth insulating layer (166) covers a terminal side portion of the element with respect to the to-be-burned member (165) for the diffusion chamber (see FIG. 31).

(12) Stacking of the Green Diffusion-Chamber-Forming Member (161)

By use of a mixture solution of secondary butanol and butyl carbitol, the green diffusion-chamber-forming member (161) prepared in <1> (1) above was stacked on and pressure-bonded to the laminate obtained through processes up to the above-described step (11), on the side on which the green positive electrode (1322) for the Ip cell was formed, such that the green positive electrode (1322) for the Ip cell was exposed.

(13) Formation of a Green Heating Resistor (12)

A mixture powder of 94 parts by mass platinum powder and 6 parts by mass alumina powder, butyral resin serving as a binder, and butyl carbitol serving as a solvent were mixed to prepare a green heating resistor paste in the form of slurry.

Figure 25:
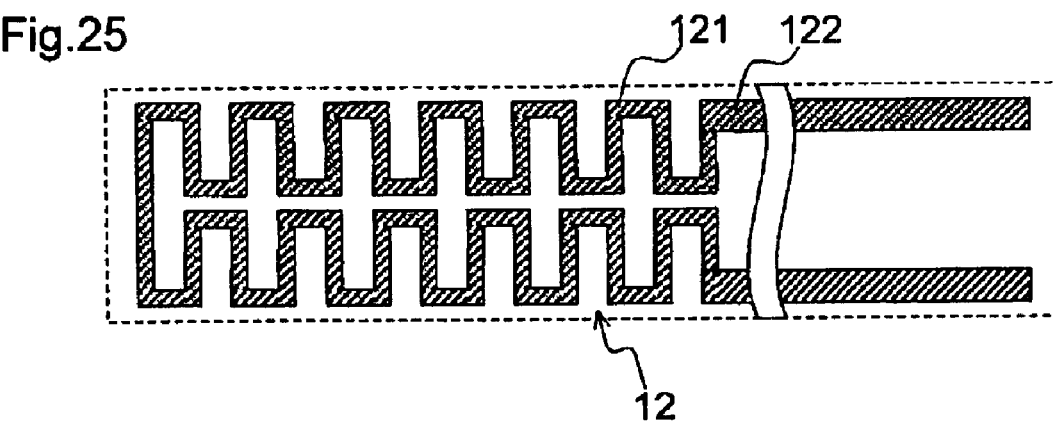
FIG. 25 is an explanatory view showing the planar shape of the green heating resistor used in the Examples.
Figure 26:
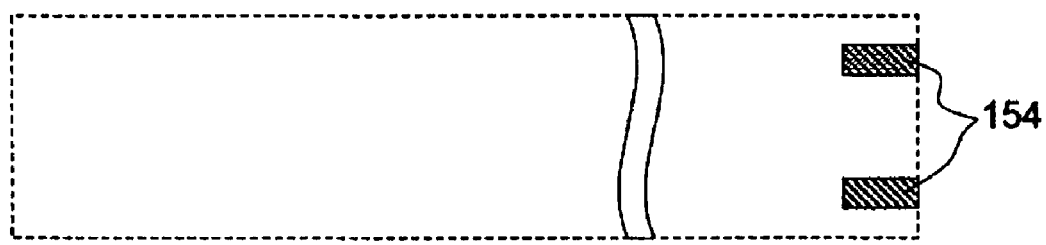
FIG. 26 is an explanatory view showing the planar shapes of the green lead electrodes for the heating resistor used in the Examples.
Figure 27:
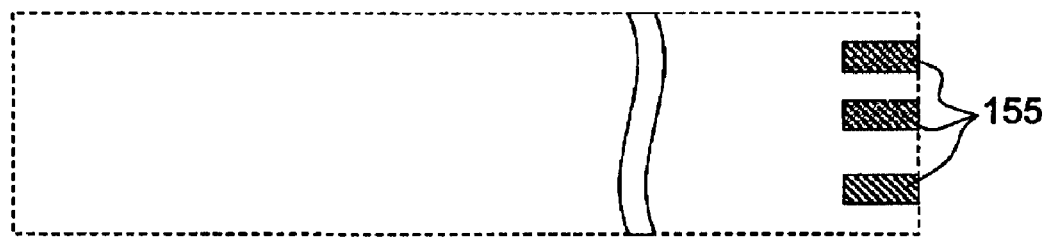
FIG. 27 is an explanatory view showing the planar shapes of the green lead electrodes for the Ip and Vs cells used in the Examples.

The thus-prepared green heating resistor paste was applied through screen printing onto the green insulative base upper layer (112) of the laminate, obtained through processes up to the above-described step (12), such that a layer of the paste (thickness of 25 μm) having a planar shape shown in FIG. 25 was formed thereon. Subsequently, the paste layer was dried to form the green heating resistor (12). After firing, this green heating resistor (12) becomes the heating portion (121) and the lead portion (122) wider than the heating portion.

(14) Stacking of the Green Insulative Base Lower Layer (111)

By use of a mixture solution of secondary butanol and butyl carbitol, the green insulative base lower layer (111) was stacked on and pressure-bonded to the laminate obtained through processes up to the above-described step (13), on the side on which the green heating resistor (12) was formed.

Thus, there was obtained a green laminate whose layers were stacked in the order shown in FIG. 31.

<3> Debinder and Firing

The green laminate obtained through processes up to the above-described step <2> (14) above was heated from room temperature to 420° C. at a rate of 10° C./hour in the atmosphere, and was maintained at 420° C. for two hours for debinding. Subsequently, in the atmosphere, the green laminate was heated to 1100° C. at a rate of 100° C./hour and then to 1520° C. at a rate of 60° C./hour, and was maintained at 1520° C. for one hour for firing. Thus, a full-range air-fuel-ratio sensor element (1) was obtained.

[2] Manufacture of a Full-Range Air-Fuel-Ratio Sensor

Figure 32:
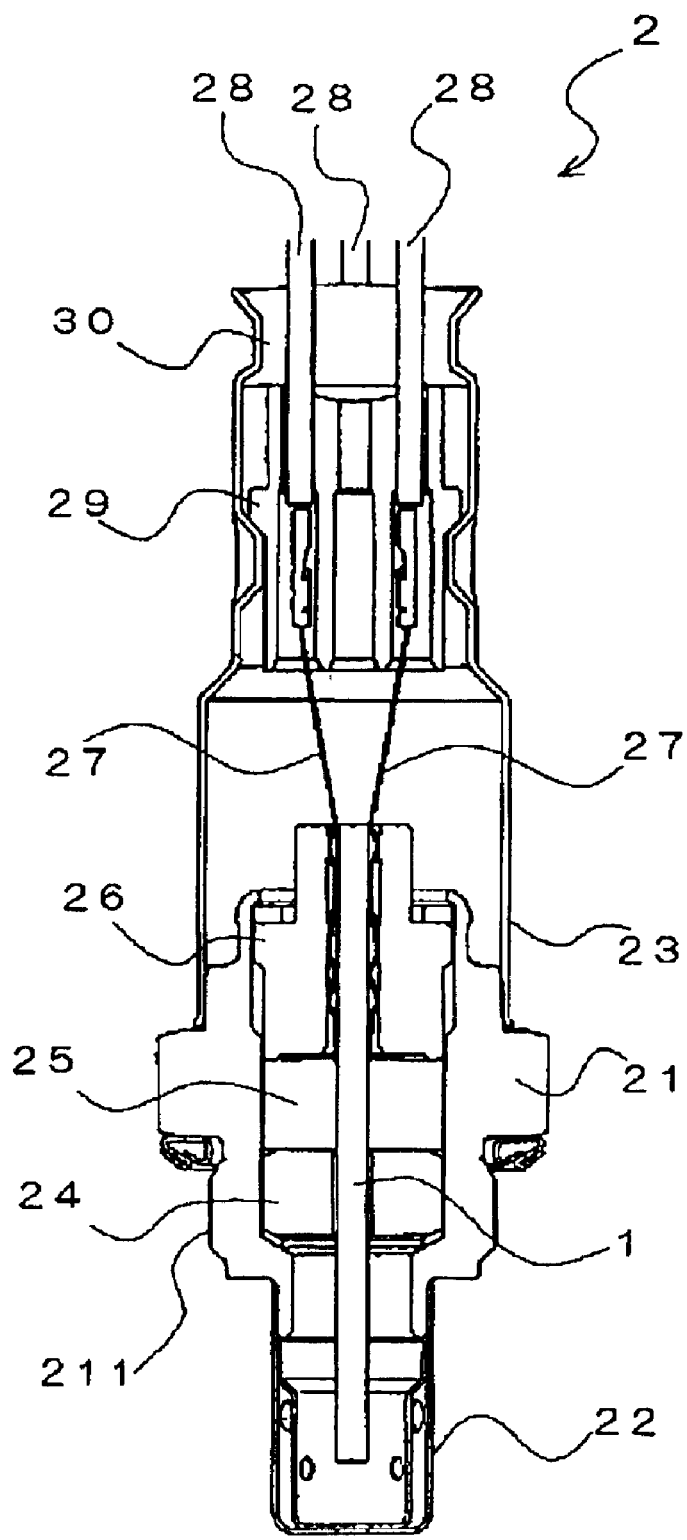
FIG. 32 is a sectional view of an example of the gas sensor incorporating the gas sensor element of the present invention.

A full-range air-fuel-ratio sensor (2) shown in FIG. 32 was manufactured by use the full-range air-fuel-ratio sensor element (1) obtained through the processes up to the above-described step [1] <3>. The upper side of the sheet of FIG. 32 corresponds to the upper side of the element, and the lower side of the sheet of FIG. 32 corresponds to the lower side of the element.

In the full-range air-fuel-ratio sensor (2), the element (1) is fixedly supported by an element holder (24) formed of alumina ceramic, a buffer material (25) made of, for example, talc powder, and a sleeve (26) formed of ceramic, which are accommodated in a metallic shell (21) having a threaded portion (211) for attaching the gas sensor to, for example, an exhaust pipe. Lead frames (27) are interposed between the sensor element (1) and the sleeve (26); and an upper end portion of the sensor element (1) is disposed within the sleeve (26). Moreover, a metallic double protector (22) which covers a lower portion of the sensor element (1) and has a plurality of holes is attached to the lower portion of the metallic shell (21). Further, an outer sleeve (23) is attached to an upper portion of the metallic shell (21). A separator (29) formed of ceramic and a grommet (30) formed of heat resistant rubber are fitted into an upper portion of the outer sleeve (23). The separator (29) and the grommet (30) have through-holes through which lead wires (28) are passed in order to connect the sensor element (1) to an external circuit.

It should further be apparent to those skilled in the art that various changes in form and detail of the invention as shown and described above may be made. It is intended that such changes be included within in the spirit and scope of claims appended hereto.

This application is based on Japanese patent application No. 2001-102383 filed Mar. 30, 2001 and is based on Japanese patent application No. 2002-97563 filed Mar. 29, 2002, the disclosures of which are incorporated herein by reference in their entirety.

What is claimed is:

1. A gas sensor element comprising an insulative base including an insulative ceramic member and a heating resistor formed on or inside the insulative ceramic member; and an oxygen pump cell and an oxygen detection cell, the cells being joined to the insulative base and each having a solid electrolyte layer and a pair of electrodes formed on a common surface of the solid electrolyte layer;

wherein said insulative ceramic member contains alumina as a predominant component and forms a diffusion-chamber-forming member having a rate-controlling introduction portion for introducing a gas to be measured; and wherein a diffusion chamber is defined by one of said pair of the electrodes of the oxygen pump cell, by one of said pair of the electrodes of the oxygen detection cell and by the diffusion-chamber-forming member containing alumina.

2. The gas sensor element as claimed in claim 1, wherein the oxygen pump cell is configured such that both the electrodes of the oxygen pump cell are disposed on the same surface of the solid electrolyte layer of the oxygen pump cell, and a partition wall containing alumina as a predominant component is provided between the electrodes such that one end of the partition wall is joined to the surface of the solid electrolyte layer.

3. The gas sensor element as claimed in claim 2, wherein the partition wall constitutes a portion of the diffusion-chamber-forming member.

4. The gas sensor element as claimed in claim 2, wherein when a portion of the partition wall within 20 $\mu$m of a plane of junction between the partition wall and the solid electrolyte layer of the oxygen pump cell is defined as a partition wall junction portion, the total amount of alkali metals, alkaline earth metals, and silicon contained in the entire partition wall junction portion is 2% by mass or less as reduced to their respective oxides.

5. The gas sensor element as claimed in claim 4, wherein when a portion of the partition wall excluding the partition wall junction portion is defined as a partition wall remaining portion, the total amount of alkali metals, alkaline earth metals, and silicon contained in the entire partition wall remaining portion is 1% by mass or less as reduced to their respective oxides.

6. The gas sensor element as claimed in claim 1, wherein the diffusion-chamber-forming member contains alumina as a predominant component.

7. The gas sensor element as claimed in claim 1, wherein the gas sensor element is fabricated by simultaneous firing of its constituent elements.

8. The gas sensor element as claimed in claim 1, wherein the solid electrolyte layer contains zirconia and alumina, and when the total amount of the zirconia and the alumina is defined as 100% by mass, the alumina content is 10 to 80% by mass, and the alumina has a mean grain size not greater than 1.0 $\mu$m.

9. The gas sensor element as claimed in claim 1, wherein the insulative ceramic member contains alumina in an amount of 70% by mass or more.

10. The gas sensor element as claimed in claim 1, wherein the insulative ceramic member contains alumina in an amount of 99% by mass or more.

11. The gas sensor element as claimed in claim 1, wherein the insulative ceramic member contains alumina in an amount of not less than 70% by mass but less than 99% by mass; the heating resistor includes a heat generation portion which generates heat upon application of voltage thereto, and a lead portion connected to the heat generation portion and having a width greater than that of the heat generation portion; and a migration prevention conductor is provided on the surface of or within the insulative base, an electrical potential maintained at the migration prevention conductor being equal to or lower than that at a boundary position between the heat generation portion and the lead portion.

12. A gas sensor including the gas sensor element as claimed in claim 1.

13. A gas sensor element comprising an insulative base (11); a heating resistor (12) formed within the insulative base (11); a plurality of solid electrolyte layers (131, 141) disposed on one face of the insulative base (11); an oxygen pump cell (13) having a pair of electrodes (1321/1322) disposed on a common surface of one solid electrolyte layer (131); an oxygen detection cell (14) having a pair of electrodes (1421/1422) disposed on a common surface of the other solid electrolyte layer (141) separated from the solid electrolyte (131); and a diffusion-chamber-forming member (161) having a rate-controlling introduction portion (163) through which a gas to be measured passes and defining a diffusion chamber (16) in cooperation with one electrode (1321) of the oxygen pump cell and one electrode (1421) of the oxygen detection cell, wherein (a) each of the insulative base (11) and the diffusion-chamber-forming member (161) contains alumina as a predominant component;

(b) a partition wall (162), extending from the diffusion-chamber-forming member (161), is joined to a surface of a solid electrolyte (131) between a pair of electrodes (1321/1322) of the oxygen pump cell (13);

(c) a boundary portion within 20 $\mu$m of a plane of junction between the solid electrolyte layer (131) and the partition wall (162) contains no portion in which the amount of substances other than alumina exceeds by 2% by mass or more the amount of substances, other than alumina, of the diffusion-chamber-forming member (161), and (d) the insulative base (11), the heating resistor (12), the solid electrolyte layers (131, 141), the electrodes (1321, 1322, 1421, 1422) and the diffusion-chamber-forming member (161) are unitarily integrated through simultaneous firing.

14. The gas sensor element as claimed in claim 13, wherein the solid electrolytes (131, 141) contain zirconia ceramic in an amount of 20 to 90% by mass and alumina in an amount of 10 to 80% by mass.

15. The gas sensor element as claimed in claim 13, wherein the insulative base (11) contains alumina in an amount of not less than 70% by mass but less than 99% by mass; the heating resistor (12) includes a heat generation portion (121) which generates heat upon application of voltage thereto, and a lead portion (122) connected to the heat generation portion and having a width greater than that of the heat generation portion; and a migration prevention conductor (152) is provided on the surface of the insulative base (11) or within the insulative base (11) such that an electrical potential at the migration prevention conductor is equal to or lower than that at a boundary position between the heat generation portion and the lead portion.

16. A gas sensor including the gas sensor element as claimed in claim 13.

* * * * *